US005801017A

United States Patent [19]

Werber et al.

[11] Patent Number: 5,801,017
[45] Date of Patent: Sep. 1, 1998

[54] **PRODUCTION OF RECOMBINANT FACTOR XA INHIBITOR OF LEECH *HIRUDO MEDICINALIS***

[75] Inventors: Moshe M. Werber, Tel Aviv; Elisha P. Zeelon, Mishmar Hashiva; Avigdor Levanon, Mohliver Street; Rachel Guy, Rehovot; Arie Goldlust, Nez-Ziona; Meir Rigbi; Amos Panet, both of Jerusalem; Meir Fischer, Rehovot, all of Israel

[73] Assignee: Bio-Technology General Corp., Iselin, N.J.

[21] Appl. No.: 226,264

[22] Filed: Apr. 8, 1994

Related U.S. Application Data

[63] Continuation-in-part of Ser. No. 45,804, Apr. 9, 1993, abandoned.
[51] Int. Cl.$^6$ .................. C07K 14/815; C12N 1/21; C12N 15/15; C12N 15/63
[52] U.S. Cl. .................. 435/69.1; 435/240.2; 435/252.3; 435/252.33; 435/320.1; 536/23.5
[58] Field of Search .................. 435/69.1, 69.2, 435/320.1, 240.2, 252.3, 252.33; 530/350, 855, 858; 536/23.5

[56] References Cited

U.S. PATENT DOCUMENTS

| | | | |
|---|---|---|---|
| 4,588,587 | 5/1986 | Gasic | 514/21 |
| 4,742,004 | 5/1988 | Hartman et al. | 435/189 |
| 4,791,100 | 12/1988 | Kramer et al. | 514/12 |
| 4,832,849 | 5/1989 | Cardin | 210/635 |
| 5,182,113 | 1/1993 | Rigbi | 424/537 |
| 5,403,596 | 4/1995 | Rigbi | 424/537 |

FOREIGN PATENT DOCUMENTS

| | | |
|---|---|---|
| 0263608 | 4/1988 | European Pat. Off. . |
| 0346894 | 12/1989 | European Pat. Off. . |
| 0352903 | 3/1994 | European Pat. Off. . |

OTHER PUBLICATIONS

Baskova et al., Chemical Abstracts, 106:60996w (1986).
Condra et al., "Isolation and Structural Characterization of a Potent Inhibitor of Coagulation Factor Xa from the Leech Haementeria ghilianii", Thrombosis and Homeostasis 61(3): 437–441.
Ferrailo, Bobbe L. and Mohler, Marjorie A., "Goals and Analytical Methodologies for Protein Disposition Studies", Protein Pharmacokinetics and Metabolism; Plenum Press. New York, 1992. pp. 1–33.
Han et al., (1989) "Cloning and Expression of cDNA Encoding Antistasin, a Leech–Derived Protein Having Anti–Coagulant and Anti–Metastatic Properties", Gene 75:47–57.
Gasic et al., Cancer Res. 44:1633–1636 (1983).
Gasic et al., Cancer Res. 44:5670–5676 (1984).
Gasic et al., Chemical Abstracts 110:185955w (1986).
Hoffman et al., (1992) "Site–Directed Mutagenesis of the Leech–Derived Factor Xa Inhibitor Antistasin", Journ. Biol. Chem., 287:943–949.
Hopp et al., (1988) "A Short Polypeptide Marker Sequence Useful For Recombinant Protein Identification And Purification", Bio/technology 6:1204–1210.
Konrad, Michael W., (1993) "The Immune System as a Barrier to Delivery of Protein Therapeutics", Biological Barriers to Protein Delivery, Plenum Press, New York. pp. 409–437.
Nutt et al., (1988) "The Amino Acid Sequence of Antistasin", Journ. Biol Chem. 263(11): 10162–10164.
Rigbi et al., (1990) Chemical Abstracts, 113:46259W
Tuszynski et al., (1987) "Isolation and Characterization of Antistasin", 262(20): 9718–9723.
Sollner, C. et al. *Eur. J. Biochem.* 219:937–943 (1994).

*Primary Examiner*—Dian C. Jacobson
*Attorney, Agent, or Firm*—John P. White

[57] ABSTRACT

The present invention provides a recombinant polypeptide having the amino acid sequence X-tyr$^{26}$-gly$^{110}$ where tyr$^{26}$-gly$^{110}$ is identical to the sequence shown in FIG. 10, and wherein X is methionine or absent and wherein asn$^{72}$ may be substituted by pro.

The invention further provides a method of producing the polypeptide which comprises transforming a host cell with an expression plasmid encoding the polypeptide, culturing the transformed host cell so that the cell produces the polypeptide encoded by the plasmid, and a method of recovering the polypeptide so produced.

27 Claims, 15 Drawing Sheets

FIGURE 6

```
a.a.#       -20                -10                  1                   11                   21
PCR4                                             YEVMYVDDPC           EDSDCEDGNK           CSPVTNECDC
11          KFWT  NFRVTFTSIL   GILFVCEILS        YEVIYVDDPC           EDSDCEDGNK           CSPVTNECDC
AS                                               <EGPFGPGC            EEAGCPEGSA           CNIITDRCTC a.a.#        31                 41                 51                   61                   71
PCR4        SPVRCRLHCN         F-YVKDSNGC         ETCAC-----           EPKCKHKNCS           TGHHCNKLTN
11          SPVRCRLHCN         F-YVKDSNGC         ETCAC-----           EPKCKHKNCP           TGHHCNKLTN
AS          SGVRCRMHCP         HGFQRSRYGC         EFCKCRLEPM           KATCDISECP           EGMMCSRLTN a.a.#        81                 91                 101                  111                  121
PCR4        KC---ELKKQ         RRMG              
11          KC---ELKKQ         RRMG              
AS          KCDCKIDINC         RKTCPNGLKR         DKLGCEYCEC           RPKRKLIPRL           S
```

FIGURE 8

```
              Met Tyr Glu Val Met Tyr Val Asp Asp Pro Cys Glu Asp    13
  1 GGA ATT CAT ATG TAT GAG GTG ATG TAT GTG GAC GAT CCA TGT GAG GAT  48

14 Ser Asp Cys Glu Asp Gly Asn Lys Cys Ser Pro Val Thr Asn Glu Cys  29
 49 TCA GAC TGT GAA GAT GGA AAC AAA TGC AGT CCT GTG ACC AAT GAA TGC  96

30 Asp Cys Ser Pro Val Arg Cys Arg Leu His Cys Asn Phe Tyr Val Lys  45
 97 GAT TGC TCT CCT GTG CGA TGC AGA TTG CAT TGC AAT TTT TAC GTC AAA  144

46 Asp Ser Asn Gly Cys Glu Thr Cys Ala Cys Glu Pro Lys Cys Lys His  61
145 GAC AGT AAT GGC TGT GAG ACA TGC GCT TGT GAG CCT AAA TGC AAG CAT  192

62 Lys Asn Cys Ser Thr Gly His His Cys Asn Lys Leu Thr Asn Lys Cys  77
193 AAA AAT TGT TCA ACT GGC CAT CAC TGC AAC AAA TTG ACA AAC AAG TGT  240

78 Glu Leu Lys Lys Gln Arg Arg Met Gly *** Thr Lys Ile *** Lys Lys  93
241 GAA TTA AAA AAG CAA CGA AGA ATG GGA TAG ACC AAA ATA TAA AAA AAA  288

94 Arg Lys Lys Leu Arg Lys Lys Asp Ser Leu Glu Ile Leu *** Arg ***  109
289 AGA AAG AAG CTG AGA AAA AAA GAT TCC CTG GAG ATT CTC TGA CGA TAA  336

110 Ile Ser Asn Ile Leu Thr Tyr Leu Phe Val Val Pro Leu Ile Asn Met  125
337 ATT AGC AAC ATA TTG ACT TAC TTA TTC GTA GTT CCG TTA ATA AAC ATG  384

126 Val Ser *** Ile Asn Ile Glu Glu Glu Leu Tyr Phe Ile Val Arg Ile  141
385 GTT TCC TAA ATA AAT ATT GAA GAA GAA CTA TAT TTT ATT GTT CGC ATA  432

142 Ser Thr Phe Lys Met Ser Lys Lys Lys Lys Lys
433 TCA ACA TTC AAA ATG TCA AAA AAA AAA AAA AAA A
```

FIGURE 10

```
  1 GAA TTC GTG AAT TCA ACA TTT CCA CAC ATA TCA AAG TAA TTT TTT TCT        48

49 AAT AAC TCA TGA GGG GTT CTC TGA GNT GCC TAC ATT CCA ATT TAA GAT        96

Met Lys    2
 97 CAA ATT TAC AAC TTT GGC ACA TTT TTG AAT AAA GGA AGC AGG ATG AAA      144

3 Phe Trp Thr Asn Phe Arg Val Thr Phe Thr Ser Ile Leu Gly Ile Leu   18
    145 TTC TGG ACG AAT TTT CGT GTC ACT TTC ACT TCC ATT TTG GGA ATT TTA  192

19 Phe Val Cys Glu Ile Leu Ser Tyr Glu Val Ile Tyr Val Asp Asp Pro   34
    193 TTC GTG TGC GAA ATT CTA TCG TAC GAA GTG ATA TAC GTG GAT GAT CCA  240

35 Cys Glu Asp Ser Asp Cys Glu Asp Gly Asn Lys Cys Ser Pro Val Thr   50
    241 TGT GAG GAT TCA GAC TGT GAA GAT GGA AAC AAA TGC AGT CCT GTG ACC  288

51 Asn Glu Cys Asp Cys Ser Pro Val Arg Cys Arg Leu His Cys Asn Phe   66
    289 AAT GAA TGC GAT TGC TCT CCT GTG CGA TGC AGA TTG CAT TGC AAT TTT  336

67 Tyr Val Lys Asp Ser Asn Gly Cys Glu Thr Cys Ala Cys Glu Pro Lys   82
    337 TAC GTC AAA GAC AGT AAT GGC TGT GAG ACA TGC GCT TGT GAG CCT AAA  384

83 Cys Lys His Lys Asn Cys Pro Thr Gly His His Cys Asn Lys Leu Thr   98
    385 TGC AAG CAT AAA AAT TGT CCA ACT GGC CAT CAC TGC AAC AAA TTG ACA  432

99 Asn Lys Cys Glu Leu Lys Lys Gln Arg Arg Met Gly *** Thr Lys Ile  114
    433 AAC AAG TGT GAA TTA AAA AAG CAA CGA AGA ATG GGA TAG ACC AAA ATA  480

115 *** Lys *** Arg Lys Lys Leu Arg Lys Asp Ser Leu Glu Ile Leu ***  130
    481 TAA AAA TAA AGA AAG AAG CTG AGA AAA GAT TCC CTA GAG ATT CTC TGA  528

131 Arg *** Ile Gly Asn Ile Cys Cys Leu Thr His Ser *** Tyr Arg Lys  146
    529 CGA TAA ATT GGC AAC ATA TGT TGT CTT ACT CAT TCA TAA TAC CGT AAA  576

147 *** Thr Trp Phe Leu Ile Ile Leu Lys Ile Asn Ile Phe Tyr Arg Ser  162
    577 TAA ACA TGG TTC CTA ATA ATA TTG AAG ATA AAT ATA TTT TAT CGT TCG  624

163 His Ile Asn Ile Gln Lys Lys Lys Lys Lys Lys Lys Lys Lys Lys Lys  178
    625 CAT ATC AAC ATT CAA AAA AAA AAA AAA AAA AAA AAA AAA AAA AAA AAA  672

179 Lys Lys Leu Glu
    673 AAA AAA CTC GAG
```

PRODUCTION OF RECOMBINANT FACTOR XA INHIBITOR OF LEECH *HIRUDO MEDICINALIS*

This application is a continuation-in-part of U.S. Ser. No. 08/045,804, filed Apr. 9, 1993, now abandoned.

BACKGROUND OF THE INVENTION

Haemostasis is the interaction of a complex series of processes aimed at ensuring the proper flow of blood through the closed, high-pressure circulatory system which comprises the mammalian vascular system. One aspect of haemostasis is the coagulation cascade which assists in maintaining the integrity of blood vessels following injury. The coagulation cascade is a complex series of processes which culminate in the formation of a fibrin clot at the site of blood vessel injury. Abnormal formation of blood clots is the cause of pathological conditions such as thrombi and embolisms.

The coagulation cascade may be initiated either through the intrinsic pathway, in which all the protein components are present in blood, or through the extrinsic pathway, in which tissue factor, a cell membrane protein, plays a critical role. The last two steps of the coagulation cascade leading to clot formation are common to both pathways. The first of these two steps comprises the formation of the "prothrombinase complex" composed of prothrombin (the zymogen of thrombin), Factor Xa (FXa), and Factor Va on the platelet's membrane surface. FXa is the enzyme which catalyzes the conversion of prothrombin to thrombin. Thrombin subsequently catalyzes the conversion of fibrinogen to fibrin, an insoluble polymer which is a major component of blood clots.

Treatment with anticoagulants is indicated in a wide range of clinical situations such as thrombosis, e.g. deep venous thrombosis (DVT), disseminated intravascular coagulation (DIC), and cardiovascular and cerebrovascular diseases.

Other indications include pathophysiological conditions associated with post operative trauma, obesity, pregnancy, side effects of oral contraceptives, prolonged immobilization particularly in the aged, and other known clinical situations involving blood coagulation.

Various references are noted by Arabic numbers in parentheses. These references are listed in numerical order at the end of the specification before the claims and are hereby incorporated by reference in their entirety to further explain the state of the art relevant to this application.

The use of anticoagulants can be beneficial in treatment of both venous thrombosis (14) such as occurs in DVT and DIC, and arterial thrombosis such as occurs during reocclusion following thrombolysis (15). The use of anticoagulants in acute coronary thrombosis is based on the established fact that the coagulation cascade is the primary cause of thrombogenicity also within platelet-rich arterial thrombi (16).

In pathological conditions of excessive clot formation, coagulation can be inhibited either by blocking the catalytic activity of thrombin by heparin—whose action is mediated by the plasmatic inhibitor antithrombin III—or hirudin, or alternatively by inhibiting an earlier step of the coagulation cascade. For example, heparinoids (low molecular weight derivatives of heparin) are known to be selective inhibitors of the step preceding thrombin, i.e., they preferentially enhance the binding of antithrombin III to FXa, thus inhibiting the FXa-catalyzed conversion of prothrombin to thrombin. Since the blood concentration of Factor X is approximately 10-fold lower than that of prothrombin, much smaller amounts of FXa inhibitors than thrombin inhibitors are required to inhibit coagulation. However, FXa usually resides in the prothrombinase complex and its activity would have to be inhibited in that complex. The inhibition by complexes of antithrombin with these heparin derivatives appears to be effective only upon free FXa in the plasma and inefficient when FXa is incorporated in the prothrombinase complex, which is the location of FXa during thrombus formation. This is similar to the disclosure that FXa in a prothrombinase complex is inaccessible to inhibition by the heparin-antithrombin III conjugate (6).

At present, heparin is the most widely used anticoagulant and anti-thrombotic drug, but it has two disadvantages: firstly, it acts at the level of thrombin inhibition, thus necessitating the administration of relatively large amounts of inhibitor; and secondly, it is likely to cause excessive bleeding due to the systemic inhibition of thrombin which is required for normal hemostasis (7). The use of hirudin and its low molecular weight analogs (hirulogs) probably entails similar disadvantages.

These disadvantages prompted the search for new anticoagulant and anti-thrombotic substances suitable for therapeutic use. The use of a selective inhibitor of FXa as an anticoagulant may reduce the problem of bleeding caused by the currently used anti-thrombotic drugs, such as heparin and hirudin and their analogs. This postulated advantage is due to the fact that a FXa inhibitor acts as a modulator of coagulation since it does not affect already existing thrombin and therefore does not completely neutralize normal hemostasis. This is because the existing thrombin is entrapped in active form in fibrin clots and is released during thrombolysis (17).

Two closely related factor Xa inhibitors have been isolated from the Mexican leech *Haementeria officinalis* (antistasin—references 1 and 2) and from the giant Amazonian leech *Haementeria ghiliani* (3, 4).

A third FXa inhibitor—termed tick anti-coagulant peptide (TAP) isolated from the tick *Ornithodorous moubata* (5,9) has been cloned, expressed, purified and characterized (10). A fourth potent FXa inhibitor, isolated from the black fly, *Simulium vittatum*, has also been characterized (11).

Both in vitro and in vivo studies have shown that inhibition of FXa-mediated coagulation with two of these inhibitors, antistasin and TAP, is as effective as heparin in preventing venous thrombosis (12).

Rigbi et al. (13) disclose a Factor Xa inhibitor isolated from the saliva of the European leech *Hirudo medicinalis*. However, Rigbi et al. do not disclose the amino acid or DNA sequences of this FXa inhibitor. Furthermore, Rigbi et al. do not teach or suggest the cloning and expression in bacteria of the FXa inhibitor isolated from the saliva of the European leech *Hirudo medicinalis* in order to obtain a biologically active polypeptide.

The present application discloses the DNA sequence encoding a FXa inhibitor (herein "FXaI") from *Hirudo medicinalis* and the corresponding amino acid sequence. The present application also discloses the cloning and expression in bacteria of recombinant FXaI and the obtaining of a biologically active recombinant polypeptide.

SUMMARY OF THE INVENTION

The present invention provides a recombinant polypeptide having the amino acid sequence X-tyr$^{26}$-gly$^{110}$ where tyr$^{26}$-gly$^{110}$ is identical to the sequence shown in FIG. 10, and wherein X is methionine or absent and wherein asn$^{72}$ may be substituted by pro.

The invention further provides a method of producing the recombinant polypeptide which comprises transforming a cell with an expression plasmid encoding the polypeptide, culturing the transformed cell so that the cell produces the polypeptide encoded by the plasmid, and a method of recovering the polypeptide so produced.

In an additional aspect, the present invention provides an antibody to the polypeptide.

This figure summarizes two different protocols used to purify the FXa inhibitor (herein "FXaI") from DLS for amino acid sequencing, and various experiments performed in order to corroborate the identity and homogeneity of the resulting preparations. In Run II, Mono-Q was used instead of Q-Sepharose.

Figure 2:
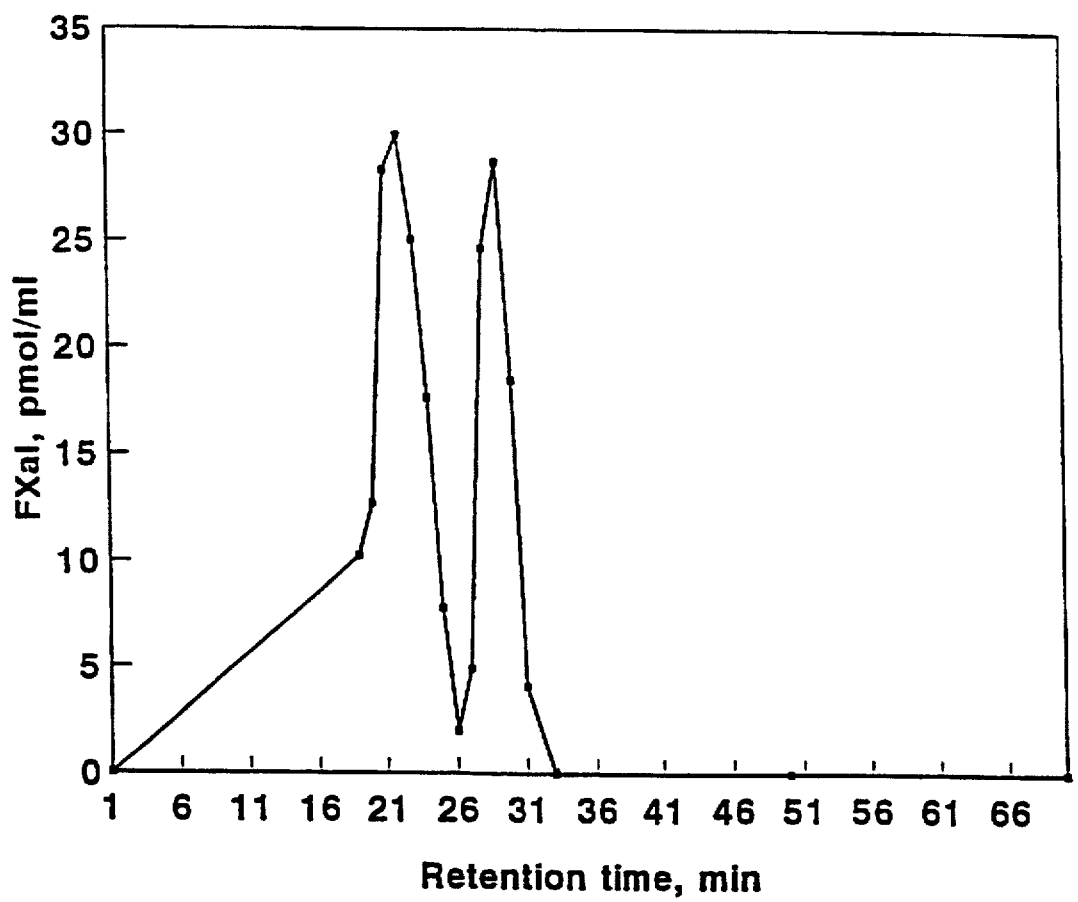

FIG. 2: Demonstration of FXaI Isoforms

This figure shows the purification of isoforms of FXaI by chromatography of DLS on a Mono-S column. DLS (100 ml) was diluted with an equal volume of the column equilibration buffer (20 mM Tris-HCl pH 7.0) and loaded at room temperature onto a 5×50 mm Mono-S column at a flow rate of 1 ml/min. The column was eluted with a 0–1M linear gradient (60 ml) of NaCl in the same buffer and washed with an additional 10 ml of 1M NaCl in the same buffer. The absorbance of the eluate was monitored at 280 nm and fractions of 1 ml were collected and assayed for FXa inhibitory activity (as described in Example 2). The chromatogram shows the concentration of FXaI (pmol/ml) in the collected fractions and clearly shows the presence of the two isoforms.

Figure 3:
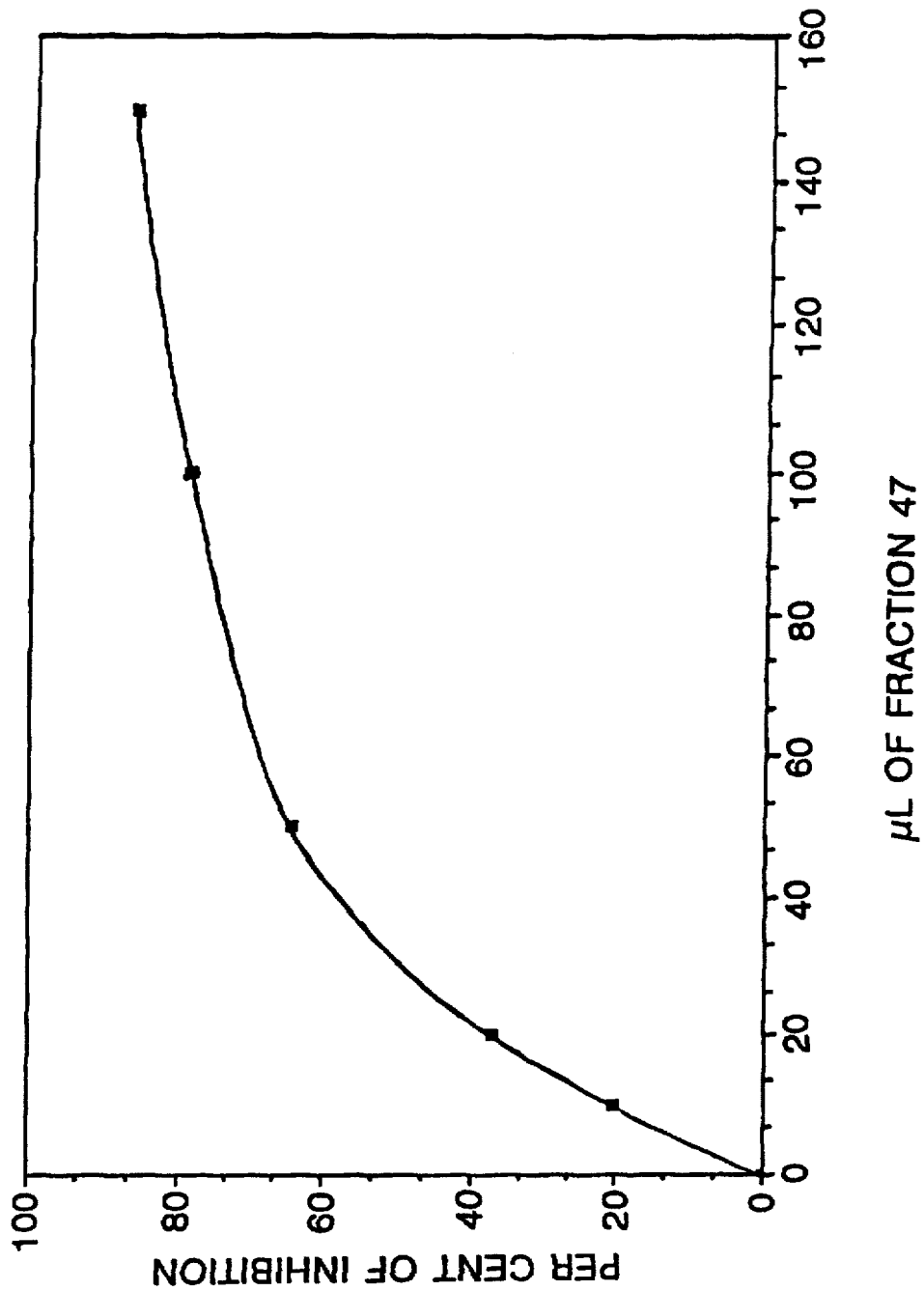

FIG. 3: Dose Response Effect of FXaI in Activity Assay

This figure shows the dose response of the inhibition of FXa by partially purified FXaI in the chromogenic assay described in Example 2. Increasing amounts of FXaI purified on Mono-Q were preincubated for 3 minutes with 2 pmol bovine FXa in a 1 ml cuvette. The initial rate of hydrolysis of the substrate CHG was monitored at 405 nm (see Example 2). Fraction 47 was the peak fraction of a particular purification experiment.

Figure 4:
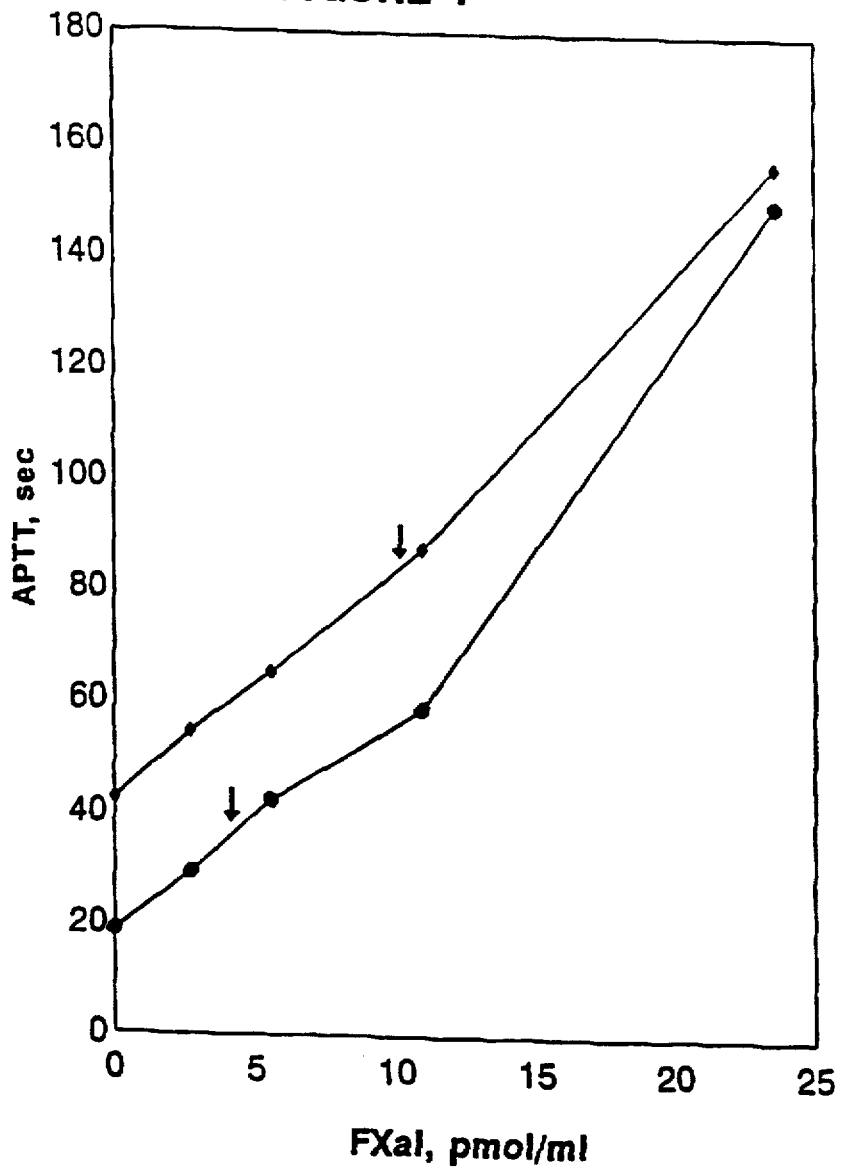

FIG. 4: Dose Response Effect of FXaI in APTT Assay

APTT (activated partial thromboplastin time) of fresh murine or human plasma was monitored by visual assessment of its clotting in the absence or presence of various amounts of FXaI. Briefly, FXaI (up to 50 µl), 100 µl of plasma and 100 µl of partial thromboplastin (Actin-FS) were incubated for 3 minutes at 37° C. The coagulation cascade was activated by the addition of 100 µl of 20 mM $CaCl_2$. The FXaI concentration in the abscissa is based on the assumption that 1 mu=1 pmol. Murine plasma—●; human plasma—♦. The arrows indicate the FXaI concentration at which doubling of the APTT is obtained.

Figure 5:
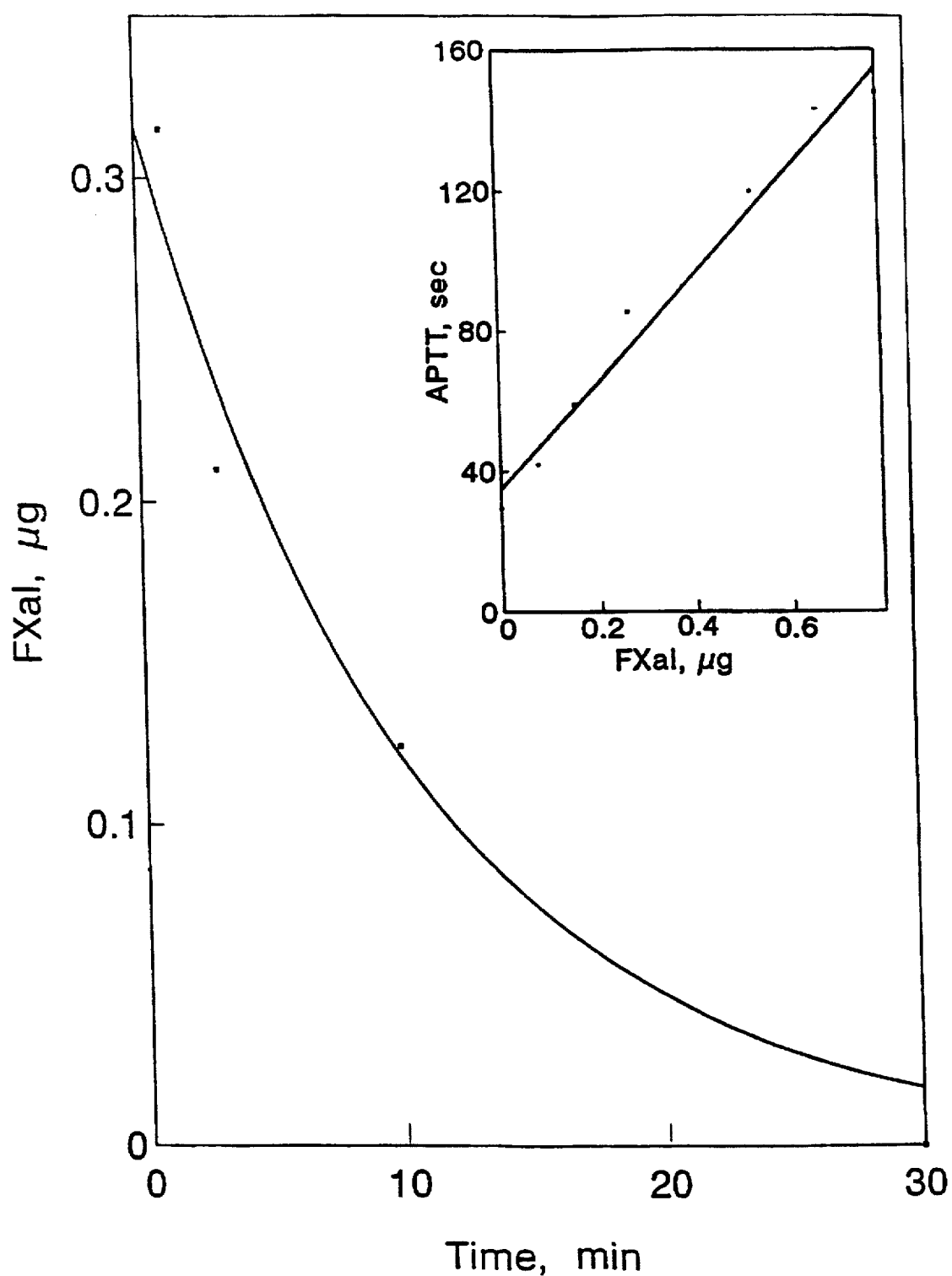

FIGS. 5A and 5B: Pharmacokinetics of FXaI in Mice

The clearance of FXaI from the blood of female mice was monitored over a period of 30 minutes by assessing the ex vivo APTT (see FIG. 4) at the time points indicated. The amount of FXaI is expressed as µg FXaI [Macart and Gerbaut, Clin. Chim. Acta 122:93–101 (1982)], determined from a calibration curve consisting of in vitro APTT time versus inhibitor concentration as shown in FIG. 5B.

FIG. 6: Amino Acid Sequence Comparison of FXaI Isolates and Antistasin

This figure compares the amino acid sequences of naturally occurring FXaI as represented by clone PCR4, cDNA clones and antistasin. The sequences were aligned by the alignment program Pileup, based on: "Simplification of Progressive Alignment Method", Feng & Doolittle, J. Mol. Evol. 35:351–360 (1987).

PCR4 SEQ. ID NO. 22 is the sequence of the PCR derived DNA sequence encoding a FXa inhibitor present in DLS and represents the sequence of the naturally occurring FXa inhibitor. (Methionine in the fourth position is apparently an error of the PCR reaction which explains why it differs from isoleucine in the fourth position of the N-terminal amino acid sequence obtained for the naturally occurring protein). PCR4 was obtained as described in Example 3 by hybridization of PCR-derived clones with the nucleotide sequence encoding the first 9 amino acids of naturally occurring FXa inhibitor isolated from leech saliva. 11 SEQ. ID NO. 23 represents the sequence of clone 11 from a cDNA library, and includes a leader or signal peptide (see Example 4). AS SEQ. ID NO. 24 represents the sequence of antistasin. "<E" represents pyroglutamate. The numbering is according to the sequence of PCR4. Gaps have been introduced to obtain the best alignment. The cysteine residues which have been aligned are highlighted.

Figure 7:
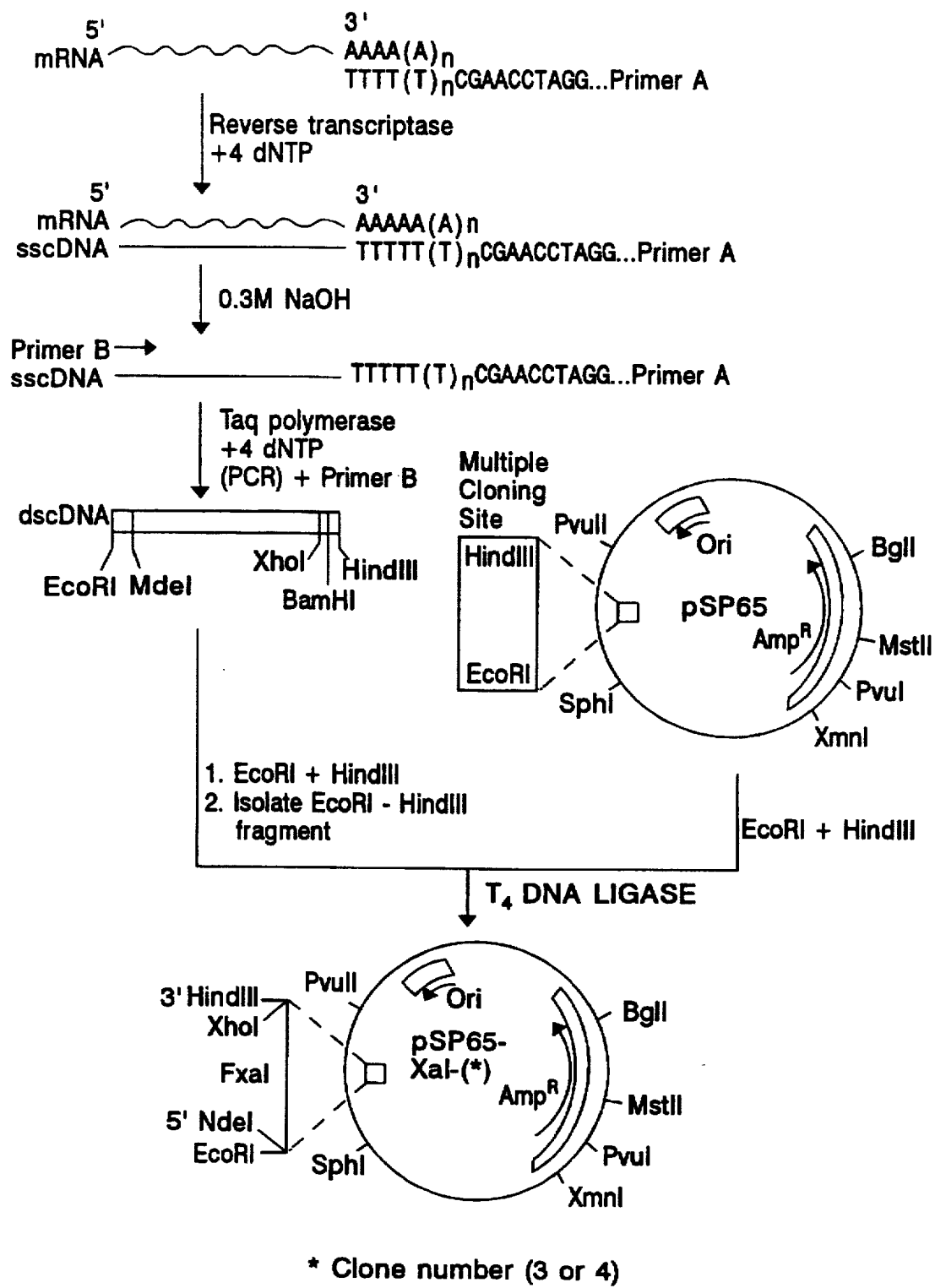

FIG. 7: Cloning of FXaI cDNA by PCR

As described in Example 3, poly $A^+$ mRNA was isolated from total RNA extracted from 120 leeches. An aliquot of the poly$^+$ mRNA so obtained (5 µg) was used as template in a reverse transcription reaction in the presence of the synthetic primer A

A: 5'-AACTCGAGGATCCAAGCTTTTTTTTTTT-TTT-3' (SEQ. ID NO. 1)

and 4 dNTPs. Following the synthesis of single stranded complementary DNA (ss-cDNA), the mRNA was degraded by overnight alkali treatment comprising 0.3M NaOH at room temperature. The neutralized ss-cDNA was subjected to PCR amplification using Taq polymerase, 4 dNTPs and the synthetic degenerative DNA oligomer B B: 5'-CCGAATTCATATGTA$_C^T$GA$_G^A$GTTATTTA$_C^T$GTI-GA$_C^T$GA$_C^T$CC-3' (SEQ. ID NO. 2)

as reverse primer.

The PCR amplification products were digested with EcoRI and HindIII. The gel purified fragments were then subcloned into the large EcoRI-HindIII fragment of plasmid pSP65. The ligation mixture was used to transform E. coli MC1061. The resulting transformants were screened by in-situ hybridization using the radiolabeled synthetic probe C (described in Example 3) corresponding to N-terminal amino acids 14 to 19 of naturally occurring FXaI.

FIG. 8: DNA and Deduced Amino Acid Sequence of Clone pSP65-XaI-4 SEQ. ID NOS. 25 and 26

Plasmid DNA was prepared from positive clones identified by in-situ hybridization with the radio-labeled probe C. Purified plasmid DNA of clone pSP65-XaI-4 was sequenced by the Sanger dideoxy method. The resulting sequence was processed using LKB 2020 DNASIS software system.

Figure 9:
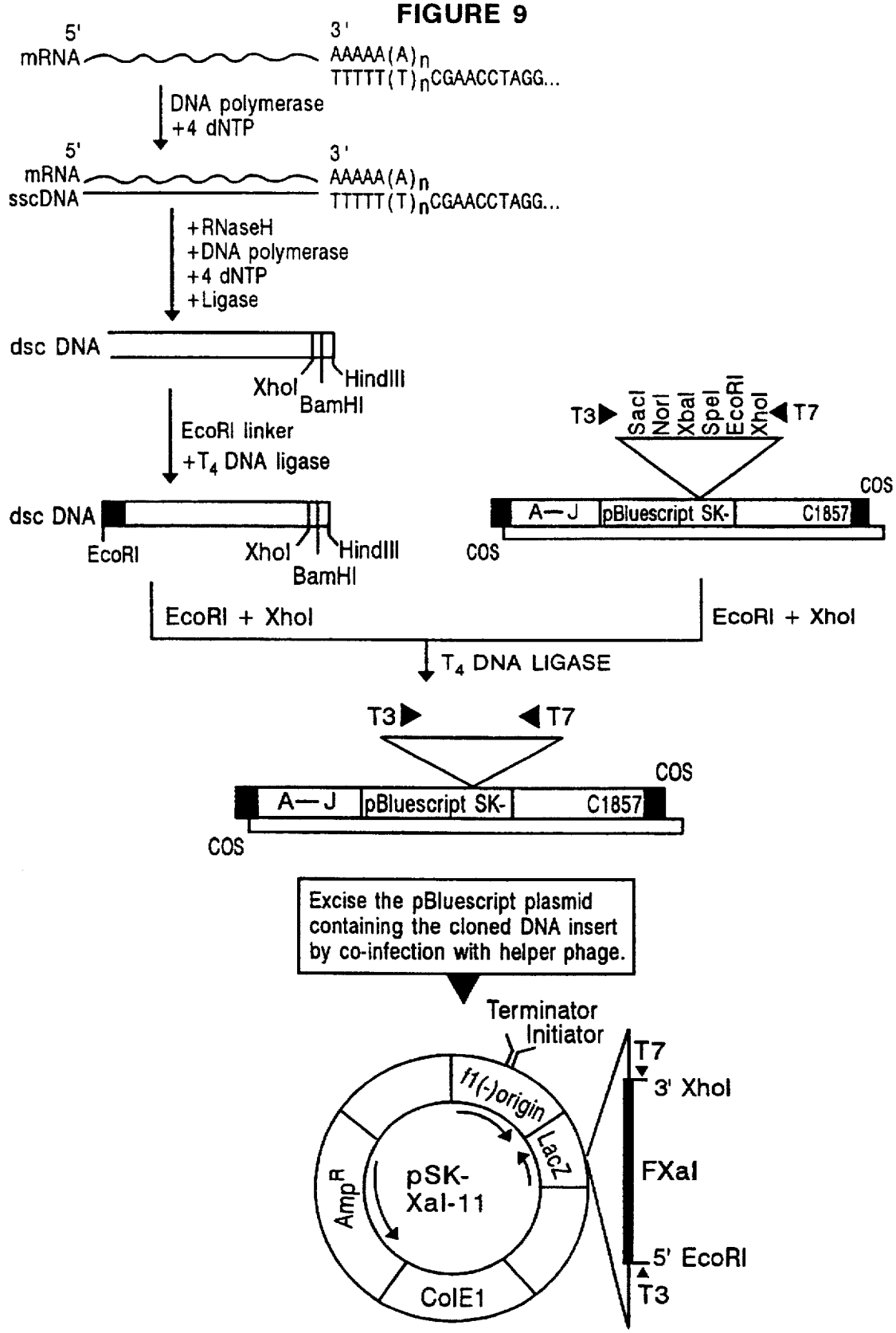

FIG. 9: Cloning of FXaI cDNA from a cDNA Library

As described in Example 4, poly $A^+$ mRNA obtained from total RNA extracted from 120 leeches was used for double stranded complementary DNA (ds-cDNA) synthesis using the Stratagene ZAP™ cDNA synthesis kit. The ds-cDNA so obtained was digested with XhoI and EcoRI and subcloned into the XhoI-EcoRI digested Uni-ZAP vector designated pBluescript SK. The cDNA library obtained was screened for FXaI cDNA clones using radiolabeled DNA of plasmid pSP65-XaI-4 as a probe, under hybridization conditions of high and low stringency. High stringency includes prehybridization of the filters for 8 hours at 60° C. in 6× SSC (1× SSC: 0.15M NaCl, 0.015M Na-citrate), 0.1% SDS, 5× Denhardt (0.1% Ficoll 400, 0.1% polyvinyl pyrrolidone, 0.1% BSA, 0.5% SDS) and 100 µg/ml salmon sperm DNA, followed by hybridization with the radioactive probe for 48 hours at 60° C. The plasmid of one of the positive clones was designated pSK-XaI-11.

FIG. 10: DNA and Deduced Amino Acid Sequences of cDNA Clone pSP65-XaI-11 SEQ. ID NOS. 27 and 28

Plasmid DNA was prepared from positive cDNA clones identified by hybridization with a radiolabeled DNA fragment from plasmid pSP65-XaI-4. Purified DNA of plasmid pSP65-XaI-11 was sequenced by the Sanger dideoxy method. The sequence obtained was processed using the LKB 2020 DNASIS software system.

Figure 11:
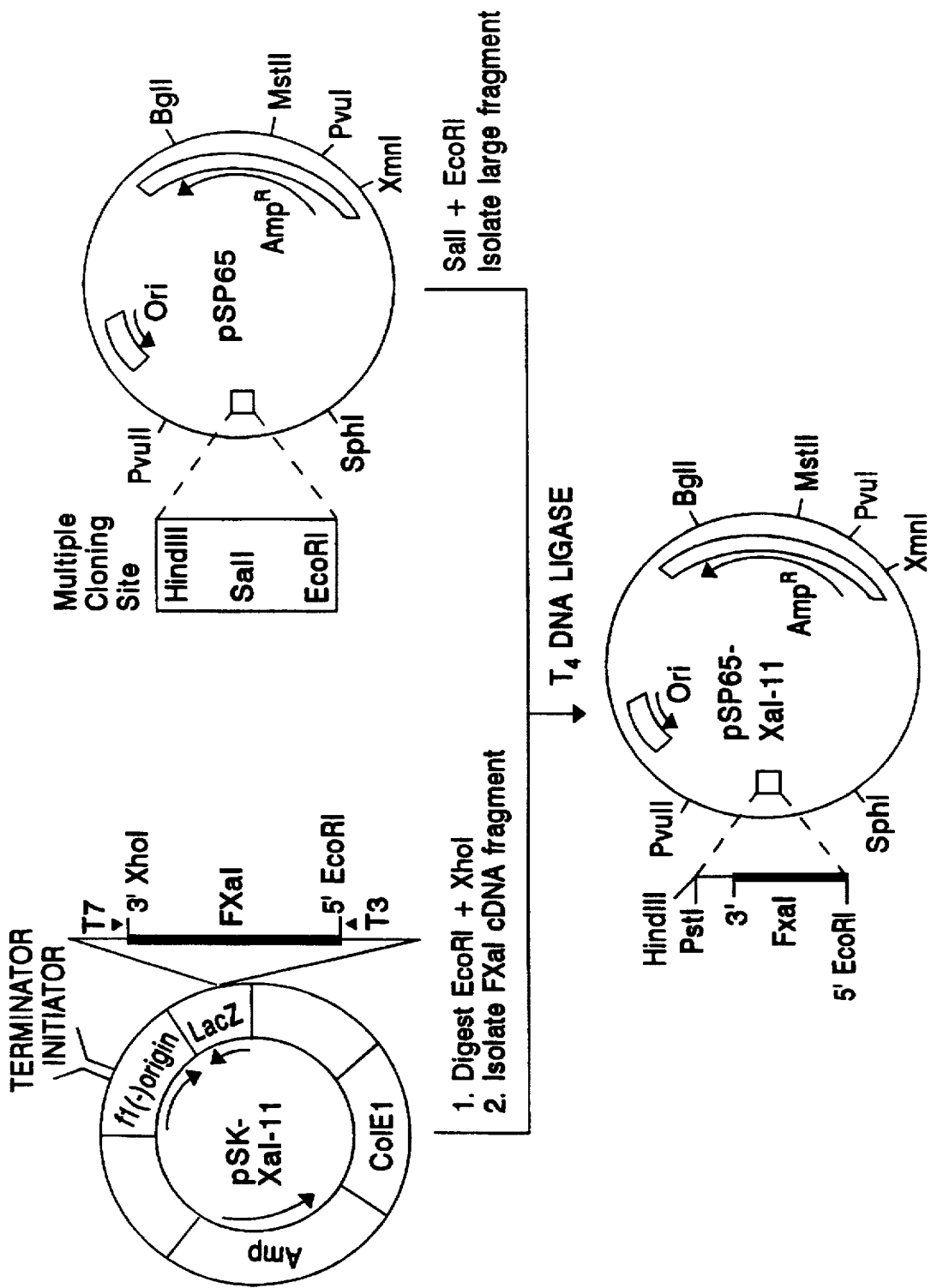

FIG. 11: Subcloning of cDNA Encoding FXaI

This figure shows the subcloning of cDNA encoding FXaI into a vector derived from plasmid pSP65. Plasmid pSK-XaI-11 was digested with XhoI and EcoRI. The XhoI-EcoRI fragment containing the FXaI coding region was isolated and subcloned into SalI-EcoRI digested plasmid pSP65. The resulting plasmid was designated pSP65-XaI-11.

Figure 12:
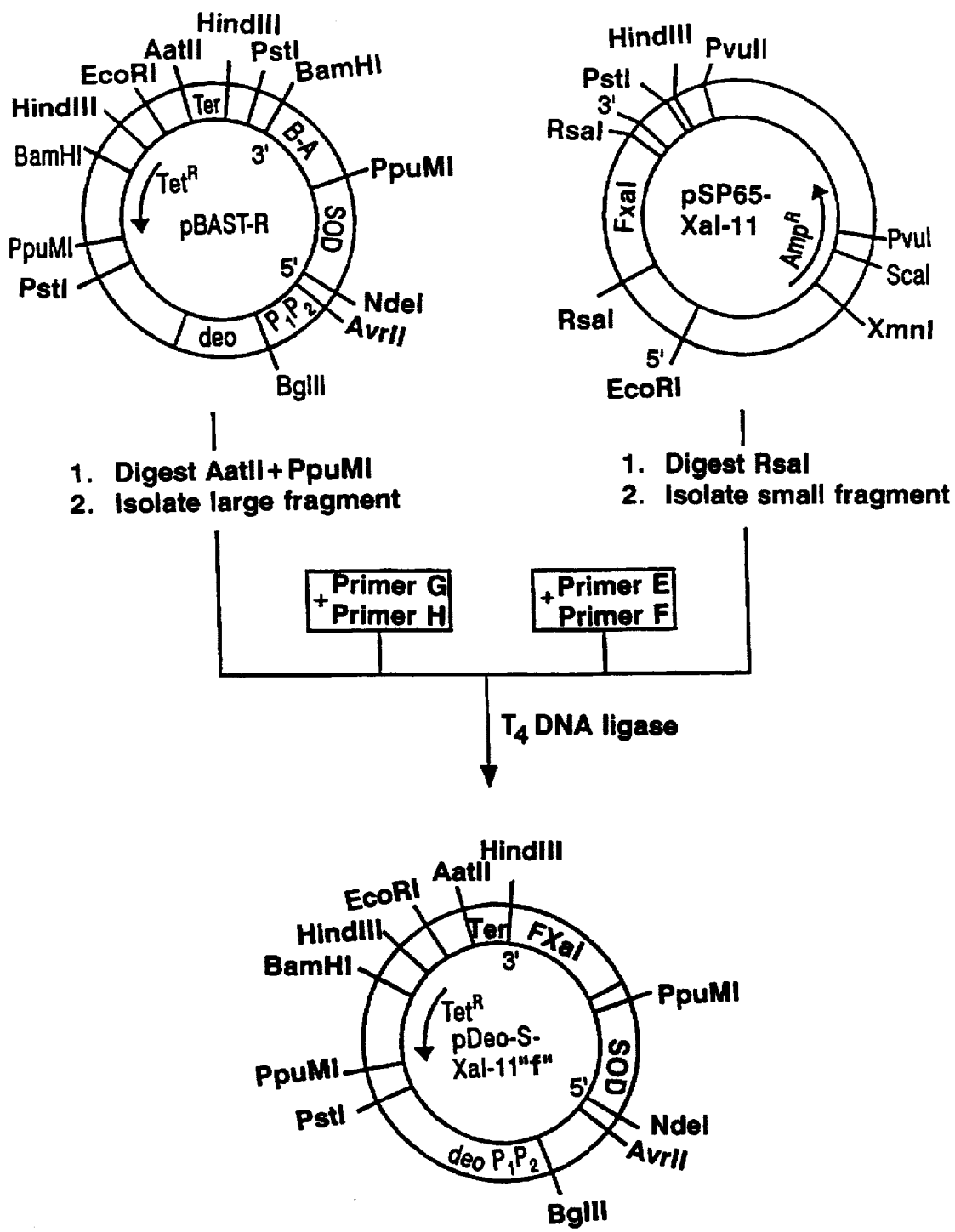

FIG. 12: Construction of Plasmid pDeo-S-XaI-11"f" for Expression of FXaI Fused to a Fragment of Human Cu/Zn-SOD This figure shows the construction of a plasmid under control of deo $P_1P_2$ for expression of recombinant FXaI produced by clone 11 fused to an N-terminal fragment of a modified Cu/Zn-SOD sequence.

Plasmid DNA pSP65-XaI-11 containing the cDNA of clone 11 was digested with RsaI. The RsaI-RsaI DNA fragment coding for FXaI was isolated and ligated to the large AatII-PpuMI fragment of plasmid pBAST-R in the presence of two sets of synthetic linkers:

```
5' end linkers:
        63Pro Met Phe Val
E: 5' - GTCCTATGTTTGTAT - 3' (SEQ. ID NO. 3)
F: 3' -     GATACAAACATA - 5' (SEQ. ID NO. 4)

3' end linkers:

G: 5' -       CGAATTCAAGCTT - 3' (SEQ. ID NO. 5)
H: 3' - TGCAGCTTAAGTTCGAA - 5' (SEQ. ID NO. 6)
```

The resulting plasmid was designated pDeo-S-XaI-11"f" and was deposited in *E. coli* 733 under ATCC Accession No. 69136.

FIG. 13: Plasmid pFSHI-6

This figure shows the structure of plasmid pFSHI-6, an expression plasmid encoding Met-His-His-His-His-His-His-Gly-Thr-Asp-Asp-Asp-Asp-Lys-FXaI (SEQ. ID NO. 7) deposited with the ATCC under ATCC Accession No. 69583.

FIG. 14: Plasmid pFSOH-11

This figure shows the structure of plasmid pFSOH-11, an expression plasmid encoding Met-His-His-His-His-His-His-Gly-Thr-Asp-Asp-Asp-Asp-Lys-Asn-Gly-FXaI (SEQ. ID NO. 8) deposited with the ATCC under ATCC Accession No. 69582.

FIG. 15: Plasmid pMLK-XaI-D-11"m"

This figure shows the structure of plasmid pMLK-XaI-D-11"m", an expression plasmid encoding an FXaI dimer deposited with the ATCC under ATCC Accession No. 69591.

DETAILED DESCRIPTION OF THE INVENTION

Abbreviations

The following abbreviations are used as amino acid designations:

| | | |
|---|---|---|
| A | Ala | Alanine |
| C | Cys | Cysteine |
| D | Asp | Aspartic acid |
| E | Glu | Glutamic acid |
| F | Phe | Phenylaline |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

The present invention provides a recombinant polypeptide (protein) having the amino acid sequence X-$tyr^{26}$-$gly^{110}$ where $tyr^{26}$-$gly^{110}$ is identical to the sequence shown in FIG. 10, and wherein X is methionine or absent and wherein $asn^{72}$ may be substituted by pro.

The recombinant polypeptide displays inhibitory activity to Factor Xa.

It is envisaged that the recombinant polypeptide of the subject invention encompasses polypeptides which are homologs of the above described polypeptide.

As used herein, a homolog of a polypeptide is a polypeptide which has substantially the same amino acid sequence and biological activity as the polypeptide.

Thus, a homolog may differ from the polypeptide of the invention by the addition, deletion, or substitution of one or more non-essential amino acid residues, provided that the resulting polypeptide retains the biological activity of the polypeptide. Persons skilled in the art can readily determine which amino acids residues may be added, deleted, or substituted (including with which amino acids such substitutions may be made) using established well known procedures, including, for example, conventional methods for the design and manufacture of DNA sequences coding for bacterial expression of polypeptide homologs of the subject polypeptide, the modification of cDNA and genomic sequences by site-directed mutagenesis techniques, the construction of recombinant proteins and expression vectors, the bacterial expression of the polypeptides, and the determination of the biochemical activity of the polypeptides using conventional biochemical assays.

Examples of homologs of the recombinant polypeptide of the subject invention are deletion homologs containing less than all the residues specified in the subject polypeptide, substitution homologs wherein one or more residues specified are replaced by other residues, and addition homologs wherein one or more amino acids residues are added to the polypeptide. All such homologs share the biological activity of the recombinant polypeptide provided by the invention.

Substantially the same amino acid sequence is herein defined as encompassing the addition or deletion of fewer than four amino acids at the N-terminus of the amino acid sequence of the polypeptide. Furthermore, there may be substitutions and/or deletions in the sequence which do not eliminate the biological activity of the protein. Such substitutions are known to those skilled in the art. Substitutions may encompass up to 10 residues in accordance with the homologous or equivalent groups described by e.g. Lehninger, *Biochemistry*, 2nd ed. Worth Pub., N.Y. (1975);

Creighton, *Protein Structure, a Practical Approach*, IRL Press at Oxford Univ. Press, Oxford, England (1989); and Dayhoff, *Atlas of Protein Sequence and Structure* 1972, National Biomedical Research Foundation, Maryland (1972).

In an additional aspect, the subject invention provides for biologically active recombinant FXaI.

Biologically active FXaI as used herein is defined as an FXaI which has inhibitory activity towards the enzymatic activity of FXa as measured by the biochemical activity assay described in Example 2. Inhibitory activity is defined as activity which lowers the enzymatic activity of Factor Xa as measured by the above mentioned biochemical activity assay.

Enzymatic activity as used herein refers to the proteolytic activity of FXa as measured by the above mentioned biochemical activity assay.

The present application discloses the purification, partial sequencing, and characterization of an FXa inhibitor (herein "FXaI") from *Hirudo medicinalis*. In another aspect, the application discloses the complete gene sequence as well as the deduced amino acid sequence of FXaI from *Hirudo medicinalis*.

In a preferred embodiment, the invention comprises a plasmid containing cDNA encoding FXaI designated pSP65-XaI-11 which was deposited under ATCC Accession No. 69138 on Dec. 1, 1992. Plasmid pSP65-XaI-11 does not express any protein since it lacks suitable regulatory elements; however, one skilled in the art knows how to manipulate the DNA of plasmid pSP65-XaI-11 in order to obtain expression of recombinant FXaI.

In more preferred embodiments, the invention provides expression plasmids for expression of recombinant FXaI. Construction of such expression plasmids is described in the following paragraphs and in the Examples.

Examples of vectors that may be used to express the nucleic acid encoding the polypeptides are viruses such as bacterial viruses, e.g., bacteriophages (such as phage lambda), cosmids, plasmids, and other vectors. Genes encoding the relevant polypeptides are inserted into appropriate vectors by methods well known in the art. For example, using conventional restriction endonuclease enzyme sites, inserts and vector DNA can both be cleaved to create complementary ends which pair with each other and are then ligated together with a DNA ligase. Alternatively, synthetic linkers harboring base sequences complementary to a restriction site in the vector DNA can be ligated to the insert DNA, which is then digested with the restriction enzyme which cuts at that site. Other means are also available.

Vectors comprising a sequence encoding the polypeptides may be adapted for expression in a range of prokaryotic and eukaryotic host cells, e.g. bacteria, fungi, yeast, insect, plant, or mammalian cells such as CHO, chicken embryo, fibroblast, kidney, and other cell lines. These vectors additionally comprise the regulatory elements necessary for expression of the cloned gene in the host cell so located relative to the nucleic acid encoding the polypeptide as to effect expression of the polypeptide. Regulatory elements required for expression include promoter and operator sequences and a ribosomal binding site. For example, a bacterial expression vector may include a promoter-operator sequence such as $\lambda P_L O_L$ or deo promoters. For initiation of translation, the $\lambda C_{II}$ or deo ribosomal binding sites may be used. Such vectors may be obtained commercially or assembled from the sequences described by methods well known in the art, for example U.S. Pat. No. 4,831,120, issued May 16, 1989 and U.S. Pat. No. 5,143,836, issued Sep. 1, 1992, which disclose methods concerning the $\lambda P_L$ promoter and European Patent Application Publication No. 303,972 published Feb. 22, 1989, which discloses methods concerning the deo promoter. Additional appropriate elements such as repressors and enhancers may also be present. Those skilled in the art know how to use regulatory elements appropriate for various expression systems.

The expression plasmids of this invention comprise suitable regulatory elements positioned within the plasmid relative to the DNA encoding the polypeptide so as to effect expression of the polypeptide in a suitable host cell, such as promoter and operators, e.g. deo $P_1P_2$ and $\lambda P_L$, ribosomal binding sites, e.g. deo and $C_{II}$, repressors and enhancers.

The regulatory elements are positioned within the plasmid relative to the DNA encoding the proteins so as to effect expression of the proteins in a suitable host cell. In preferred embodiments of the invention, the regulatory elements are positioned close to and upstream of the DNA encoding the proteins. Other suitable regulatory elements are known to those skilled in the art.

In one embodiment, the expression plasmid is plasmid pDeo-S-XaI-11"f" deposited under ATCC Accession No. 69136 on Dec. 1, 1992. In another embodiment, the expression plasmid is plasmid pFSHI-6 deposited under ATCC Accession No. 69583 on Mar. 11, 1994. In yet another embodiment, the expression plasmid is plasmid pFSOH-11 deposited under ATCC Accession No. 69582 on Mar. 11, 1994. In yet another embodiment, the expression plasmid is plasmid pMLK-XaI-D-11"m" deposited under ATCC Accession No. 69591 on Mar. 22, 1994.

Those skilled in the art will understand that the plasmids deposited in connection with this application may be readily altered by known techniques (e.g. site-directed mutagenesis or insertion of linkers) to encode expression of related polypeptides. Such techniques are described for example in Sambrook, J., Fritsch, E. F. and Maniatis, T. (1989) Molecular Cloning: A Laboratory Manual, 2nd edition, Cold Spring Harbor Laboratory Press.

The expression plasmids of the invention may be introduced into suitable host cells, preferably bacterial host cells. However, those skilled in the art will understand that the expression plasmids of this invention may be suitably modified for introduction into a range of procaryotic and eucaryotic host cells as described above.

Preferred bacterial host cells are *Escherichia coli* cells. Examples of suitable *Escherichia coli* cells are strains 733 for plasmids under control of the deo promoter and 4300 or 4300 (F−) for plasmids under control of the $\lambda P_L$ promoter, but other suitable *Escherichia coli* strains and other bacteria can also be used as hosts for the plasmids. An example of a eukaryotic cell is an insect cell. Preferred insect cells are Sf-9 cells harboring a baculovirus expression system. The bacteria used as hosts may be any strains including auxotrophic (such as A1645), prototrophic (such as A4255), and lytic strains; F+ and F− strains; strains harboring the cI[857] repressor sequence of the $\lambda$ prophage such as A1645 and A4255); and strains devoid of the deo repressors and/or the deo gene (see European Patent Application Publication No. 0303972, published Feb. 22, 1989). *Escherichia coli* strain A4255 has been deposited under ATCC Accession No. 53468, and *Escherichia coli* strain Sø930 has been deposited under ATCC Accession No. 67706. In preferred embodiments, *E. coli* 4300 is used as host for expression plasmids under control of $\lambda P_L$ and *E. coli* 733 is used as host for expression plasmids under control of the deo promoter.

The invention provides a bacterial cell which comprises these expression plasmids. In one embodiment, the bacterial cell is an *Escherichia coli* cell. In a preferred embodiment, the invention provides *E. coli* strain 733 containing plasmid pDeo-S-XaI-11"f" deposited with the ATCC under ATCC Accession No. 69136. In another preferred embodiment, the invention provides *E. coli* strain 4300 containing plasmid pFSOH-11 deposited with the ATCC under ATCC Accession No. 69582. In yet another preferred embodiment, the invention provides *E. coli* strain 4300 containing plasmid pFSHI-6 deposited with the ATCC under ATCC Accession No. 69583.

All the *E. coli* host strains described above can be "cured" of the plasmids they harbor by methods well-known in the art, e.g. the ethidium bromide method described by R. P. Novick in *Bacteriol. Reviews*, 33:210 (1969).

In another aspect the present application discloses the presence of a novel and previously unknown isoform of the naturally occurring FXaI, herein designated isoform B. Isoform B of the FXaI has the same N-terminal amino acid sequence as isoform A (the previously disclosed isoform of the FXaI), though it appears to behave somewhat differently on SDS-PAGE and column chromatography.

The proteins of the subject application may be obtained as "mature" proteins, i.e. in the absence of any extension or fusion peptides, as prepeptides containing extension peptides (e.g. leader peptide), or as fusion peptides containing all or a portion of another protein or polypeptide.

In one embodiment, a fusion protein is produced comprising FXaI and 63 N-terminal amino acids of a modified Cu/Zn-SOD sequence. Cu/Zn-SOD is described in coassigned U.S. Pat. No. 4,742,004 and by Steinman, H. M., *Superoxide Dismutase*, (Oberley, ed.) CRC Press, Florida, pages 11–68, (1982).

Other precursors of recombinant FXaI may also be obtained by fusion with other proteins (e.g. Nilsson et al., Current Opinion in Structural Biology 2:569–575 (1992) and Hopp et al., BioTechnology 6:1204–1210 (1988)).

Mature protein may be obtained by direct expression or by cleavage of a fusion protein or prepeptide. Additional methods of obtaining the mature recombinant FXaI are known to those skilled in the art.

In addition, the subject invention provides expression plasmids encoding the recombinant proteins described above. In a preferred embodiment, the invention provides an expression plasmid designated pDeo-S-XaI-11"f" deposited under ATCC Accession No. 69136 on Dec. 1, 1992. In another embodiment, the expression plasmid is plasmid pFSHI-6 deposited under ATCC Accession No. 69583 on Mar. 11, 1994. In yet another embodiment, the expression plasmid is plasmid pFSOH-11 deposited under ATCC Accession No. 69582 on Mar. 11, 1994. In yet another embodiment, the expression plasmid is plasmid pMLK-XaI-D-11"m" deposited under ATCC Accession No. 69591 on Mar. 22, 1994.

In a further embodiment, the invention provides a host-plasmid system comprising a host cell and an expression plasmid containing DNA encoding FXaI.

In a preferred embodiment, the host cell is an *E. coli* cell and the plasmid is pDeo-S-XaI-11"f". In a more preferred embodiment, the host cell is *E. coli* 733.

In other preferred embodiments, the host cell is an *E. coli* cell and the plasmid is pFSHI-6 or plasmid pFSOH-11 or plasmid pMLK-XaI-D-11"m". In a more preferred embodiment, the host cell is *E. coli* 4300.

One skilled in the art knows how to produce the polypeptides disclosed herein from different plasmids and/or different nucleotide sequences encoding the same amino acid sequences due to the degeneracy of the genetic code. One skilled in the art can also produce substantially identical homologs having small changes in the amino acid sequence which do not affect the structure or specific biological activity of the polypeptide. Such homologs are also encompassed by the invention.

In another aspect, the present application discloses production in bacteria of FXaI from *Hirudo medicinalis*, and their refolding to yield active protein having inhibitory activity towards the enzymatic activity of FXa identical or similar to that of naturally occurring FXaI. FXaI as used herein refers to a protein isolated from dilute leech saliva (DLS) of the leech *Hirudo medicinalis* and any corresponding recombinant protein which has the activity of inhibiting FXa.

The invention provides a method of producing the polypeptide which comprises transforming a host cell with an expression plasmid encoding the polypeptide, culturing the transformed host cell so that the cell produces the polypeptide encoded by the plasmid, and a method of recovering the polypeptide so produced.

In a preferred embodiment, the invention provides a method for producing the purified biologically active recombinant FXaI polypeptide wherein the host cell is a bacterial cell, and the recovering comprises:

(a) disrupting the cells so as to produce a lysate containing the polypeptide;

(b) treating the lysate so as to obtain inclusion bodies containing the polypeptide;

(c) treating the inclusion bodies so as to obtain the polypeptide in soluble form;

(d) treating the resulting soluble polypeptide so as to form biologically active polypeptide;

(e) recovering the biologically active polypeptide so formed; and (f) purifying the biologically active polypeptide so recovered.

In preferred embodiments, the treating of step (c) comprises the addition of a denaturant, the treating of step (d) comprises contacting the polypeptide with a mixture of a thiol-containing compound and a disulfide, and the purifying of step (f) comprises column chromatography.

In more preferred embodiments, the denaturant is guanidinium chloride or urea, the thiol containing compound is glutathione, thioredoxin, β-mercaptoethanol, or cysteine, the disulfide is oxidized glutathione, cystine, or the product of air oxidation of mercaptoethanol, and the column chromatography comprises either one or both of Q-Sepharose chromatography and Heparin-Sepharose chromatography.

In one embodiment, the polypeptide of step (a) is a dimer.

In another embodiment, following step (c) the polypeptide is subjected to enzymatic cleavage to produce recombinant FXaI.

In yet another embodiment, following step (d) the polypeptide is subjected to enzymatic cleavage to produce recombinant FXaI.

In preferred embodiments, the enzymatic cleavage comprises CNBr cleavage.

The subject invention further provides a method of producing recombinant FXaI which comprises:

(a) culturing a host cell containing a plasmid containing DNA encoding FXaI attached to an extension peptide, so that the DNA directs expression of the resulting FXaI prepeptide;

(b) recovering from the cell the FXaI prepeptide so expressed;

(c) subjecting the FXaI prepeptide to enzymatic cleavage to produce recombinant FXaI;

(d) purifying the recombinant FXaI.

In a preferred embodiment, step (b) further comprises:
(i) disrupting the host cell so as to form a suspension comprising cell debris and a protein supernatant solution;
(ii) separating said cell debris from the soluble protein supernatant solution;
(iii) purifying the FXaI prepeptide from the supernatant by column chromatography;

In yet another embodiment, step (c) further comprises cleaving the FXaI prepeptide with enterokinase or hydroxylamine.

In another embodiment, step (iii) further comprises DEAE-Sepharose or Q-Sepharose chromatography.

In yet another embodiment, the chromatography is followed by metal affinity chromatography and dialysis.

The invention further provides a composition comprising any of the polypeptides of the subject invention effective to obtain a desired therapeutic effect resulting from the biological activity of the polypeptide, and a suitable carrier.

In a preferred embodiment, the desired therapeutic effect is the reduction of the extent of blood coagulation. The extent of blood coagulation may be represented by in vitro coagulation assays such as APTT.

The invention also provides a method of reducing the extent of blood coagulation comprising contacting the blood with an amount of the polypeptide effective to reduce the extent of blood coagulation.

In a preferred embodiment, the contacting is effected in vivo in a subject. In a more preferred embodiment, the subject suffers from excessive blood coagulation.

In particular embodiments, the subject suffering from excessive blood coagulation has a condition selected from the group consisting of vascular disorders, post-operative trauma, tendency towards venous thromboembolism associated with obesity, pregnancy, the use of oral contraceptives, and prolonged immobilization.

Accordingly, the invention provides a method of reducing the extent of blood coagulation in a cerebrovascular disorder such as stroke or other cerebrovascular disorders.

The invention provides a method of reducing the extent of blood coagulation in a condition of excessive blood coagulation such as occurs in thrombosis, more particularly venous thrombosis and more particularly deep venous thrombosis or disseminated intravascular coagulation.

The invention further provides a method of reducing the extent of blood coagulation in a condition of excessive blood coagulation such as occurs in arterial thrombosis such as thrombosis of a coronary artery.

As described above, thrombosis often recurs following thrombolysis. Accordingly, the invention provides a method of reducing the extent of blood coagulation following thrombolysis. In a preferred embodiment, the thrombolysis is effected with a fibrinolytic agent. In particular embodiments, the fibrinolytic agent is tissue plasminogen activator, or streptokinase. The polypeptide may be administered before, during, or after the administration of the fibrinolytic agent, or bound to the fibrinolytic agent.

The invention also provides a method of inhibiting the activity of Factor Xa which comprises contacting Factor Xa with an amount of the polypeptide effective to inhibit the activity of the Factor Xa.

In an additional embodiment, the polypeptide of the invention may be used to prevent recurrent influenza infection. Influenza infection is a dynamic process comprising infection and reinfection of cells by the virus. The activation enzyme implicated in A-type influenza infection has been shown to be very similar to chicken blood coagulation Factor Xa (Gotoh B. et al. (1990), EMBO J. 9:4185–4190 and Ogasawara T. et al. (1992), EMBO J. 11: 467–472). It is therefore possible that the corresponding human FXa is involved in influenza infections occurring in humans.

It is envisioned that an inhibitor of FXa would be useful in preventing recurrent influenza infection. In a specific embodiment, the FXa inhibitor would be the polypeptide of the invention. It is also contemplated that the polypeptide might be administered in conjunction with additional therapeutic agents. In a particular embodiment, the additional therapeutic agent comprises an oxygen free radical scavenger. In a preferred embodiment, the oxygen free radical scavenger is superoxide dismutase. In still more preferred embodiments, the superoxide dismutase is Cu/Zn-SOD (co-assigned U.S. Pat. No. 4,742,004) or MnSOD (coassigned U.S. Ser. No. 842,740, filed Feb. 27, 1992 and co-assigned UK Patent No. GB 2,183,658, Apr. 25, 1990).

Such treatment would have numerous advantages over presently available therapeutic and prophylactic methods of handling influenza infection. Presently used methods of influenza prevention are based on immunization against the influenza virus. This method has proved unreliable due to the high frequency of mutation of the influenza virus, as well as the large number of viral strains.

Use of an inhibitor of the mechanism of infection would therefore be greatly advantageous in comparison to presently available vaccines by not being based on the immunological properties of the viral particle, and therefore not limited to a particular viral strain.

Furthermore, since influenza is a bronchopulmonary disease, the treatment would preferably be administered as an aerosol, thus providing a simple method of administration.

In an additional aspect, the invention provides an antibody which specifically reacts with an epitope of the polypeptide. In a particular embodiment, the antibody is a monoclonal antibody. The invention also encompasses a polypeptide which competitively inhibits the specific reacting of the antibody.

Plasmids and Strains Deposited in Connection with the Present Invention

Various plasmids and E. coli strains useful in carrying out the methods of the invention were deposited on Dec. 1, 1992 with the American Type Culture Collection, 12301 Parklawn Drive, Rockville, Md. 20852 pursuant to and in satisfaction of, the requirements of the Budapest Treaty on the International Recognition of the Deposit of Microorganisms for the Purposes of Patent Procedure.

The plasmids and strains deposited on Dec. 1, 1992 include plasmid pSP65-XaI-11 deposited in E. coli MC1061 under ATCC Accession No. 69138 which contains cDNA encoding FXaI of clone 11; plasmid pDeo-S-XaI-11"f" deposited in E. coli 733 under ATCC Accession No. 69136 which expresses FXaI fused to 63 N-terminal amino acids of a modified sequence of human Cu/Zn-SOD under control of the deo promoter; and E. coli 733 which is a host cell for plasmids controlled by the deo promoter, deposited as noted above under ATCC Accession No. 69136.

Additionally, plasmid pMLK-100, a vector harboring the $\lambda P_L$ promoter, was deposited in E. coli 4300 under ATCC Accession No. 68605 on Feb. 6, 1991.

Furthermore, plasmids FSHI-6 and pFSOH-11 were deposited in E. coli 4300 under ATCC Accession Nos. 69583 and 69582 respectively on Mar. 11, 1994.

In addition, plasmid pMLK-XaI-D-11"m" was deposited in E. coli 4300 under ATCC Accession No. 69591, on Mar. 22, 1994.

Many difficulties, as will be described in the following paragraphs, had to be overcome in order to obtain the N-terminal sequence of the naturally occurring polypeptide, clones encoding the polypeptides of the present application, expression of the polypeptides in bacteria, and recombinant proteins having the biological activity and specificity of the naturally occurring protein.

Firstly, it was extremely difficult to obtain sufficient protein from *Hirudo medicinalis* for purification and characterization because of (a) the small size of the organism; (b) the tiny amounts of the protein present in this leech due to the requirement of the organism for only minute quantities of the protein; (c) the difficulty of obtaining a sufficient amount of DLS not contaminated by large amounts of hemoglobin (which seriously impairs the purification process); and (d) the significant degree of heterogeneity observed in the isolated proteins, both in terms of variability in amino acid sequences, i.e., isoforms, and in post-translational modifications. This last aspect may in part be due to the necessity of isolating protein from a large number of organisms due their small size, and thereby introducing factors of natural genetic variation.

For example, in order to obtain the amount of purified FXaI required for N-terminal sequencing (i.e., approximately 100 pmol), it was necessary to "milk" 300 leeches and to process between 1–2 liters of dilute leech saliva (DLS), containing only about 0.14 µg/ml of FXaI with a yield of 10–25%.

In contrast, the amount of purified Factor Xa inhibitor obtained from salivary gland extract of the Mexican leech, *Haementaria officinalis* (antistasin), was of the order of 12 µg/ml (0.3 mg per 25 ml) of salivary gland extract (1). This is nearly 100-fold more than the concentration of the protein present in DLS of *Hirudo medicinalis*. Similarly, large amounts of the Factor Xa inhibitor isolated from the giant Amazonian leech, *Haementaria ghiliani* (3), which is at least twice as big as the Mexican leech were obtained from the salivary gland extract of only 14 organisms.

Secondly, the crude protein extract had to be purified and sequenced and the homogeneity and the identity of the resulting protein proved.

Thirdly, although antibodies against antistasin failed to recognize a cross-reacting molecule in extracts from *H. medicinalis* (3), it still had to be established unequivocally that FXaI is indeed different from antistasin.

Lastly, it was necessary to establish that the purified FXa inhibitory fraction did not contain a "latent" N-terminal blocked antistasin-like contaminant, migrating to the same position as FXaI on Tricine SDS-PAGE.

EXAMPLES

The Examples which follow are set forth to aid in understanding the invention but are not intended to, and should not be construed so as to, limit its scope in any way. The examples do not include detailed descriptions for conventional methods employed in the isolation of cDNA, the construction of vectors, the insertion of genes encoding polypeptides of interest into such vectors, or the introduction of the resulting plasmids into bacterial hosts. Such methods are well known to those skilled in the art and are described in numerous publications including Sambrook, Fritsch, and Maniatis, *Molecular Cloning: A Laboratory Manual*, 2nd Edition, Cold Spring Harbor Laboratory Press, USA, (1989).

EXAMPLE 1

Purification of FXaI of *H. medicinalis*

FXaI was purified from *Hirudo medicinalis* dilute leech saliva (DLS). DLS was obtained as described by Rigbi et al., Comp. Biochem. Physiol. 87B:567–573 (1987).

In brief, a phagostimulatory solution of 0.001M arginine in saline kept at 37° C. was placed over a washed membrane (sausage skin, obtained from Nippi Gelatin Casing, Tokyo, Japan) which was stretched across a cylinder open at both ends. Starved leeches were allowed to suck the solution into their crop until satiated. As the feeding solution was not stirred, it is assumed that most of the saliva excreted into it was reimbibed. Following cessation of feeding, the ingested solution containing the saliva was forced out through the mouth by squeezing the leech from the posterior end forwards. Colorless fluid, which was named dilute leech saliva (DLS) was collected.

Figure 1:
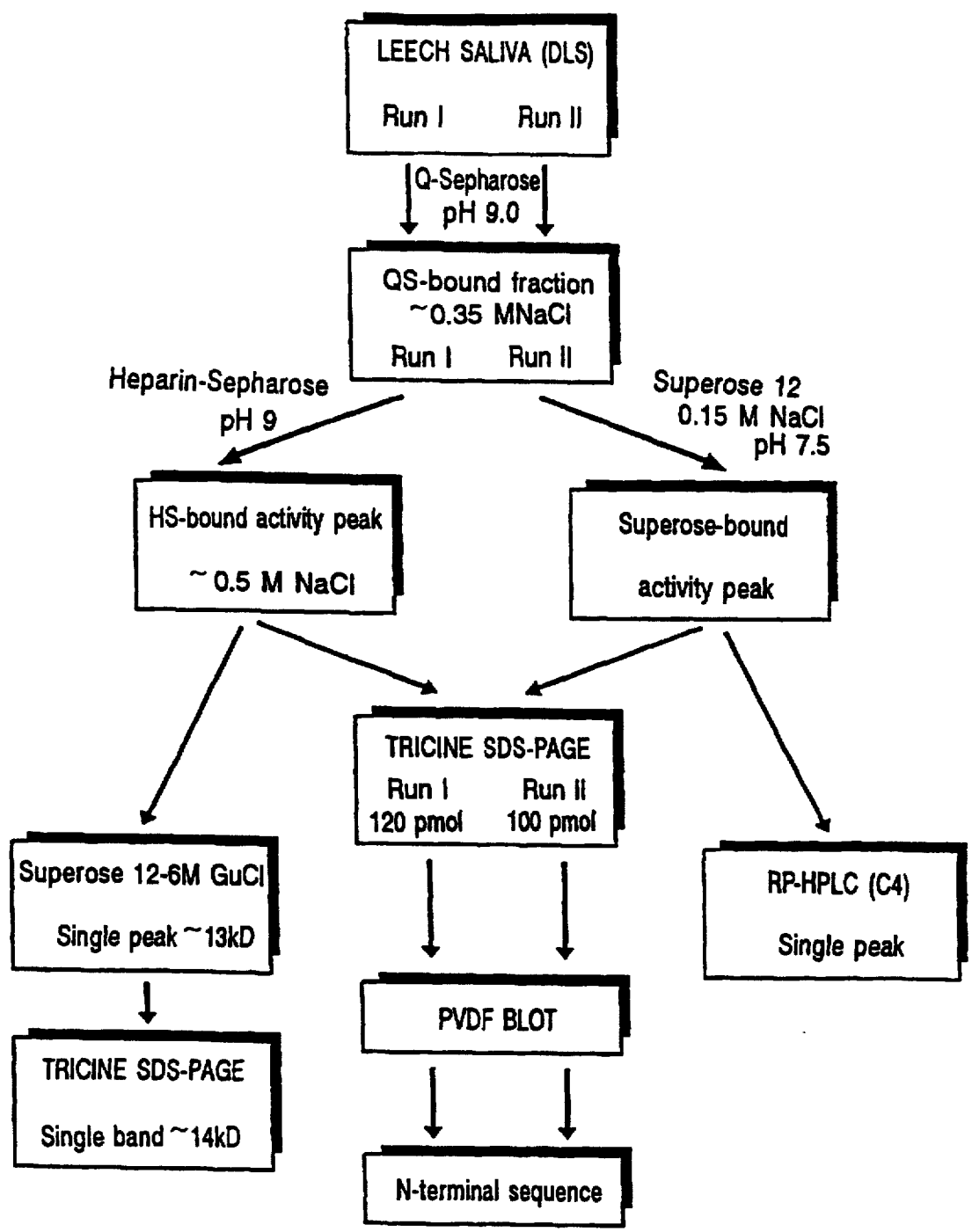
FIG. 1: Purification and Identification of FXaI

Two methods of purification of the proteins from DLS will be described below. The methods are similar and consist of anion exchange chromatography on a quaternary aminomethyl column (Mono-Q or Q-Sepharose) followed by either gel filtration chromatography on Superose 12 or by affinity chromatography on Heparin-Sepharose. In both cases, the identity and the homogeneity of the preparation were verified by Tricine SDS-PAGE and at least one supplementary method. These purification protocols are summarized in FIG. 1.

1. Purification on Mono-Q followed by Superose 12

DLS obtained from about 25 leeches (150 ml) was diluted with an equal volume of 20 mM Tris-HCl pH 8.9, and applied to an FPLC Mono-Q column (5×50 mm). The column was eluted with a linear gradient of 0–0.5M NaCl in the same buffer (80 ml) at a flow rate of 1 ml/min. Absorbance was monitored at 280 nm. The column was then washed with a second linear gradient of 0.5M–1M NaCl in the same buffer (20 ml) and at the same flow rate followed by an additional 5 ml of 1M NaCl. Fractions of 1 ml were collected and assayed for both FXaI and hirudin activities. The FXaI activity peak eluted at about 0.35M NaCl and was separate from the hirudin activity peak. The fractions containing FXa inhibitory activity were pooled and applied to a Superose 12 column 10×900 mm (three 10×300 mm columns in series). Elution was carried out at room temperature with 20 mM Tris-HCl pH 8 containing 150 mM NaCl at a flow rate of 0.3 ml/min. Absorbance was monitored at 280 nm. FXaI eluted under these conditions as a single peak with an apparent molecular weight of 4 kD. In contrast, electrophoresis of the purified FXaI on Tricine SDS-PAGE revealed a single band of molecular weight of about 14 kD. As will be described in Example 2, this inconsistency in molecular weight determination may be due to nonspecific interactions of the Superose 12 with the FXaI leading to retardation of elution of the FXaI from the column.

The purified protein was also analyzed by reverse phase HPLC (RP-HPLC) as follows. The FXaI purified on Superose 12 was dialyzed against water, lyophilized, redissolved in 1 ml of 0.1% trifluoroacetic acid (TFA), and loaded onto a 7µ RP-300 column (Aquapore, Brownlee Labs) attached to a Kontron Model 420/422S HPLC. Elution was carried out with a linear gradient of 0–100% acetonitrile in 0.01% TFA (60 ml) at a flow rate of 1 ml/min. Absorbance was monitored at 220 nm. A single peak with a retention time of 38.51 minutes was observed thus demonstrating that the FXaI was purified to homogeneity.

2. Purification on Q-Sepharose followed by Heparin-Sepharose

DLS obtained from about 50 leeches (320 ml) was diluted with an equal volume of 20 mM Tris-HCl pH 8.9, and applied to a Q-Sepharose column (10×50 mm). The column was eluted with a linear gradient of 0–0.5M NaCl in the same buffer (70 ml) at a flow rate of 1 ml/min; absorbance was monitored at 280 nm. The column was then washed with 1M NaCl in the same buffer at the same flow rate. Fractions of 1 mL were collected and assayed for both FXaI activity and hirudin activity. This verified that the FXaI peak was indeed separated from the hirudin peak. The FXaI eluted in a single peak at about 0.35M NaCl, which was similar to the elution from Mono-Q described above. The fractions containing FXaI activity were pooled and dialyzed against 20 mM Tris-HCl pH 8.9. An aliquot of 7 ml was then applied to a Heparin-Sepharose column (10×50 mm). Elution was carried out with a linear gradient of 0–0.5M NaCl in the same buffer (70 ml) at a flow rate of 1 ml/min and absorbance monitored at 280 nm. The column was then washed with 1M NaCl in the same buffer and at the same flow rate. Fractions of 1 mL were collected and assayed for FXaI activity. The purified FXaI eluted in a single peak at about 0.30M NaCl. By this protocol, the FXaI was purified approximately 600-fold with an overall yield of 14%. As will be described below, Tricine SDS-PAGE analysis of this preparation revealed a single band with a molecular weight of 14 kD. The homogeneity of FXaI purified by this procedure was further verified by gel permeation chromatography on Superose 12 under denaturing conditions.

EXAMPLE 2

Characterization of Purified FXaI Isolated From DLS

1. Molecular Weight
1.1 Tricine SDS-PAGE

Various preparations of FXaI prepared as described in Example 1 were analyzed to evaluate both the degree of homogeneity and the molecular weight of the protein. The protocol used was a modified version of the method of Schagger et al. (Anal. Biochem. 166:368–379 (1987)). The FXaI band ran at approximately 14 kD and in some cases as a broader band of about 12–14 kD. The significance of the 12–14 kD band will be discussed below.

1.2. Gel Permeation Chromatography on BioGel P-60

Molecular weight was also determined by gel permeation chromatography of a crude preparation of FXaI on BioGel P-60. FXaI activity eluted at a retention time corresponding to a molecular weight of 14 kD. As mentioned above, the molecular weight of the FXaI as determined under denaturing conditions by electrophoresis on Tricine SDS-PAGE was also 14 kD, thus demonstrating that FXaI is a 14 kD monomer.

1.3 Behavior of FXaI Under Denaturing and Non-denaturing Conditions

As described above, in the course of the purification, FXaI was purified from contaminating proteins by gel permeation chromatography on Superose 12 under non-denaturing conditions. Under these conditions, it was found that the FXaI activity eluted as a single peak at a retention time corresponding to an apparent molecular weight of 4 kD. However, when the same sample was run under denaturing conditions on Superose 12 in the presence of 6M guanidinium chloride (GuCl) the FXaI activity eluted as a single peak at a retention time corresponding to about 13 kD. Upon removal of the denaturant by dialysis, this peak was found to regain biological activity, and Tricine SDS-PAGE revealed the usual single 14 kD band. These results suggest that under non-denaturing conditions there may exist some non-specific interactions between FXaI and the Superose 12 which leads to some retardation of the protein on the column.

2. N-terminal Sequence of FXaI 2.1 N-terminal Sequence of Purified Naturally Occurring FXaI Samples of FXaI purified by the two procedures described in Example 1 were further resolved by Tricine SDS-PAGE and electroblotted onto a PVDF membrane. The membrane slice containing FXaI was subjected to automatic sequencing (Applied Biosystems Microsequencer, Model 475A) for 20 cycles. In both cases the following sequence was obtained:

Y— E— V—I— Y— V— D— D— P — C*— E— D— S— D—
Tyr—Glu—Val—Ile—Tyr—Val—Asp—Asp—Pro—Cys—Glu—Asp—Ser—Asp—

C*— E— D— G— N— K
Cys—Glu—Asp—Gly—Asn—Lys  (SEQ. ID NO. 9)

*Cysteines are not detected by this method of amino acid sequencing and were later deduced from the DNA sequence.

2.2 N-terminal Sequence of Naturally Occurring FXaI Treated with Pyroglutamate Aminopeptidase The N-terminal sequence of FXaI was also determined on naturally occurring protein treated with pyroglutamate aminopeptidase.

FXaI was subjected to pyroglutamate aminopeptidase treatment by the following procedure. FXaI (20 µg) was incubated for 6 hours at 4° C. with pyroglutamate aminopeptidase (2 µg dissolved in 100 µl of 100 mM sodium phosphate buffer pH 8 containing 5 mM DTT, 10 mM EDTA and 5% glycerol). Thereafter, another aliquot of pyroglutamate aminopeptidase (2 µg) was added and the reaction was allowed to proceed for another 15 hours at room temperature.

The N-terminal sequence obtained following pyroglutamate aminopeptidase treatment was identical to that obtained without pyroglutamate aminopeptidase treatment, indicating, that, unlike antistasin, no FXaI isoform is blocked by pyroglutamate at its N-terminus.

3. Polymorphism of FXaI
3.1 Purification of FXaI Isoforms on Q-Sepharose

During large scale purification of FXaI from several liters of DLS, two peaks of activity were obtained upon elution from the Q-Sepharose column. For example, 2450 ml of DLS were diluted two-fold in 20 mM Tris-HCl buffer pH 8.9, and applied to a 60 ml Q-Sepharose column (2.5×12.2 cm). Elution was carried out with a linear gradient of 0–0.5M NaCl in the same buffer (360 ml) at a flow rate of 3 ml/min, followed by a second linear gradient of 0.5M–2M NaCl in the same buffer (360 ml) and at the same flow rate. A broad activity peak was eluted by the first gradient (0–0.5M NaCl) and a narrower peak containing about 30% of the total FXaI activity loaded onto the column was eluted by the second gradient (0.5–2M). The activity-containing fractions from each peak were pooled separately, and the peaks corresponding to elution by the low salt and high salt gradients were designated isoform A and isoform B respectively. The pooled peaks corresponding to isoform A and isoform B were then applied separately to a 10 ml Heparin Sepharose column and eluted with two linear NaCl gradients (40 ml each) as above. Isoform A eluted from the Heparin-Sepharose column in the first gradient, i.e., between 0 and 0.5M NaCl, whereas isoform B eluted in the second gradient, i.e., between 0.5 and 1M NaCl. This is similar to the elution profile from Q-Sepharose. Isoform A migrated on Tricine SDS-PAGE with an apparent molecular weight of 13–14 kD, whereas isoform B migrated with an apparent molecular weight of 11–12 kD. These results correspond to the broad 12–14 kD molecular weight band observed upon electrophoresis of a homogeneous preparation of FXaI as described above in Section 1.1.

The difference in molecular weight between isoforms A and B was corroborated by chromatography on a Superose 12 gel permeation column (flow rate 0.4 ml/min), equilibrated in 6M GuCl/20 mM Tris-HCl pH 7.8 (as in Section 1.3). The position of the two isoforms was detected by monitoring the FXaI activity of the fractions following dialysis to remove the denaturant. Additionally, a sufficient amount of isoform B was isolated from the Superose 12 column to enable its detection on Tricine SDS-PAGE where it migrated to a position corresponding to molecular weight of 11–12 kD. This is similar to the result obtained with isoform B eluted from Heparin-Sepharose.

3.2 Purification of FXaI Isoforms on Mono-S

DLS (100 ml) was diluted with an equal volume of 20 mM Tris-HCl pH 7, and applied to an FPLC-attached Mono-S cation exchanger column (5×50 mm). Elution was carried out at room temperature with a linear gradient of 0–1M NaCl in the same buffer (60 ml) at a flow rate of 1 ml/min and washed with an additional 10 ml of 1M NaCl in the same buffer. Absorbance was monitored at 280 nm. Fractions of 1 ml were collected and assayed for FXaI activity. Two peaks of activity were found (FIG. 2), which further corroborates the results shown above.

3.3 Characterization of Isoform B

In order to verify that the peak designated isoform B is indeed an isoform of FXaI, an aliquot of isoform B, purified on Q-Sepharose and Heparin-Sepharose as described above (section 3.1) was applied to a Mono-Q column. The FXaI activity eluted at a high salt concentration (about 0.6M NaCl) as previously observed on Q-Sepharose. The purified protein was then electrophoresed on Tricine SDS-PAGE and electroblotted onto a PVDF membrane for N-terminal amino acid sequencing of 9 cycles (see Example 1, section 2.1). The 9 amino acid sequence so obtained was identical to that found for isoform A which would seem to indicate that isoform A and isoform B have the same amino acid sequence.

Since isoform B and isoform A seem to have the same amino acid sequence, the difference in behavior of the two isoforms on column chromatography and on SDS-PAGE is probably attributable to post-translational modifications such as glycosylation.

4. Glycosylation and Sugar Analysis

FXaI was shown to stain as a glycoprotein by dot blot analysis, using a method based on the substrate staining of alkaline phosphatase-hydrazide bound to periodate-modified sugars (Gershoni et al., Anal. Biochem. 146:59, 1985).

The differences in glycosylation between the two FXaI isoforms were analyzed according to a known procedure (Egger and Jones, J. Chromat. 33:123–131, 1985). Isoforms A and B of FXaI purified from DLS were subjected to hydrolysis in sealed vials at 105° C. for 8 hours using 2M trifluoroacetic acid (TFA). The TFA was then removed by lyophilization. The hydrolysates and sugar standards were then derivatized with dansyl hydrazine. 0.1M acetic acid in 0.1% TFA was used as a solvent instead of TCA, thus avoiding the need for partial purification on Sep-Pak cartridges. Following derivatization, the samples were lyophilized, dissolved in 20% acetonitrile, and subjected to HPLC analysis (Beckman, model 110A or Kontron, model 420/422S) using a Supelco LC-8 column (250×4.6 mm, particle size 5μ). Elution was monitored at 254 nm, using a UV detector (Jasco, model 875-UV or Kontron HPLC detector, model 430).

The results are presented in Table 1 and show that isoforms A and B differ in the degree and type of glycosylation. This may explain their differing behavior on ion-exchange columns.

TABLE 1

Monosaccharide Analysis of FXaI Isoforms

| Sample | Retention time (min) | Sugar content μg/sample |
| --- | --- | --- |
| Glucuronic acid* | 8.29 | — |
| Isoform A<sup>a</sup> | 9.15 | 0.26 |
|  | 15.20 | 5.96 |
| Isoform B<sup>b</sup> | 7.65 | 3.55 |
|  | 11.38 | 19.54 |
|  | 14.52 | 18.11 |
|  | 17.21 | 3.18 |
| Galactose* | 10.47 | — |

*Standard
<sup>a</sup>5 μg protein
<sup>b</sup>4 μg protein

5. Quantitation and Assay of FXaI
5.1 Biochemical Activity Assay

The assay of FXa inhibitory activity is based on the inhibition of the FXa-mediated hydrolysis of the chromogenic substrate methoxycarbonyl-D-cyclohexylglycyl-glycyl-arginyl p-nitroanilide (CHG) as described below.

FXa activity is observed as the increase in absorbance at 405 nm ($\epsilon_M=9920$ M$^{-1}$cm$^{-1}$), due to the release of p-nitroaniline. The kinetic parameters for hydrolysis of this substrate by FXa are as follows: catalytic constant=130 sec$^{-1}$ and $K_m=15$ μM. The appropriate substrate concentration was determined from the molar absorbance which is 8210 at 342 nm. The reaction mixture contains 50 mM Tris-HCl pH 8.2, 5 mM CaCl$_2$, 200 mM NaCl, 0.1% PEG, 40 μM substrate, and approximately 2 nM FXa. The FXa concentration is determined more precisely from the initial (first 20 seconds) rate of CHG hydrolysis at 40 μM in the absence of inhibitor based on the kinetic parameters mentioned above.

Inhibition of the increase in absorbance may be observed in the presence of the FXa inhibitory activity of an FXa inhibitor such as FXaI of the present invention. The inhibitor concentration is the difference in absorbance between the reaction in the presence and absence of inhibitor multiplied by the FXa concentration.

This determination assumes the formation of a 1:1 enzyme-inhibitor complex, and further assumes that the dissociation constant is low enough (i.e., tight binding) to enable essentially total binding of the inhibitor (FXaI) to the enzyme (FXa). In fact, the saturation shape of the dose-response curve (FIG. 3) provides evidence that a finite and not negligible dissociation of the inhibitor-enzyme complex occurs under these conditions. The dose response curve is represented by the degree of inhibition versus FXaI concentration and is further described in Section 5.2.

The degree of dissociation of the FXa-FXaI complex is characterized by the inhibition constant ($K_i$) and may be determined from the inhibited velocity of the hydrolysis of the chromogenic substrate CHG. These results may be analyzed according to kinetic schemes of competitive inhibition for enzyme-inhibitor complexes, essentially as described in Dixon and Webb, *Enzymes* (3rd ed.), Academic Press, New York, (1979). The $K_i$ of naturally occurring FXaI in the chromogenic assay is about 9 nM.

The determination of inhibitor concentration determined by the above method is therefore probably underestimated. It was found useful to define the FXaI concentration as the protein concentration ($IC_{50}$) required to obtain a constant degree of inhibition, usually 50% and to define the amount causing 50% inhibition under these reaction conditions to be 1 milliunit (mu) or 1 pmol. $IC_{50}$ is generally higher than Ki, and depending on the type of inhibition, can be shown to depend variously on substrate concentration, Ki, Km and other factors (Segel, L (1974) "Enzyme Kinetics", Wiley Interscience). In fact, the range of values of $IC_{50}$ was determined to be about 10–20 nM.

The FXaI activity assay used to determine concentration during purification and characterization was performed in an Elisa Titertek Twin Reader, Type 380 (EF LAB). The final activity measurement of purified protein was also performed in a Phillips (model PU 8720) UV/Vis scanning spectrophotometer.

5.2 Type of Inhibition and Dose-response Curve

Almost complete saturation of the degree of inhibition in the chromogenic assay is obtained with increasing amounts of partially purified naturally occurring FXaI (FIG. 3). However, the degree of inhibition achieved is time-dependent, and almost no inhibition is observed without preincubation of the FXa and FXaI for several minutes (3–5 min) at room temperature. This behavior is typical of slow-binding inhibitors and has been previously described for antistasin (reference 8). Even a high inhibitor concentration does not seem to achieve complete inhibition of FXa activity. This may indicate that besides the dissociation of the enzyme-inhibitor complex, a complex is also formed between enzyme, inhibitor and substrate, as in mixed-type inhibition. Mixed-type inhibition has been previously reported for naturally-occurring FXaI (13) and antistasin (8).

5.3 Coagulation Assay

The inhibitory activity of FXaI was also assayed as the increase of the activated partial thromboplastin time (APTT) essentially as described in Spaethe, *Haemostasis*, AHS/Deutschland GmbH, Munich (1984), using as reagent Actin FS (Dade), which contains ellagic acid for activation of Factors XII and Factor XI, and soy bean phospholipid. Under these conditions, and in the presence of 20 mM $CaCl_2$, only the intrinsic pathway of coagulation is activated.

Isoform A (the major fraction of naturally occurring FXaI isolated from DLS) was used in these experiments. Its activity in the chromogenic assay was 164 mu/ml which is equivalent to 164 pmol/ml, assuming tight binding between FXa and the inhibitor (see Section 5.1 above). The protein concentration of this batch was assayed by SDS-Bradford (Macart and Gerbaut, Clin. Chim. Acta 122:93–101 (1982)) and was determined to be ~20 µg/ml.

APTT was assessed in human and murine plasma (both fresh and frozen). In human plasma a concentration of 10 mu/ml caused doubling of the APTT, whereas in murine plasma 3.5 mu/ml was sufficient to achieve the same effect (FIG. 4). Based on protein concentration, these values are equivalent to 87 and 30 nM respectively. No difference was observed between fresh and frozen plasma of either kind.

5.4 Assay of FXa Inhibitory Activity in the Prothrombinase Complex

The inhibitory activity of FXaI may also be assayed by its effect on FXa in a prothrombinase complex. The phospholipid used was rabbit brain cephalin (Sigma). The contents of one vial, suspended in 1 ml 0.15M NaCl were diluted 1:40 in the reaction mixture, i.e. 2.5 µl/100 µl. The concentrations of the other components were: FXa 250 pM, prothrombin 2.67 µM, FVa 4.2 nM and $Ca^{++}$ 1 mM in 20 mM Tris-HCl pH 7.4/150 mM NaCl/0.1% polyethylene glycol 6000. Following 10 minutes of preincubation at 37° C., the reaction was initiated by the addition of prothrombin. Aliquots were removed at various time intervals. The reaction was stopped by 10 mM EDTA and aliquots were kept on ice until assayed. The inhibition of FXa by a FXa inhibitor (e.g. FXaI of the present invention) was observed as the effect of FXaI on the generation of thrombin from prothrombin at 37° C. The amount of thrombin generated was assayed using 80 µg of the synthetic thrombin p-nitroanilide substrate S-2238 (KabiVitrum, Sweden) at 23° C.

The results obtained for naturally occurring FXaI were $K_i$ of 72 pM and $IC_{50}$ of 190 pM. The $IC_{50}$ is higher because, as described above, it does not take into account the dissociation of the inhibitor-enzyme complex.

In some later experiments, some slight modifications were made to the protocol of the prothrombinase complex assay: the assay mixture contained 50 pM FXa and 1.35 µM prothrombin instead of 250 pM FXa and 2.67 µM prothrombin, resulting in a Ki of 120 pM.

6. Inhibitory Activity of FXaI (i) Inhibition of FXa

The inhibition constants of naturally occurring FXaI were determined in the chromogenic assay and in the reconstituted prothrombinase complex assay as described above.

(ii) Inhibition of Trypsin

Inhibition of bovine trypsin by naturally occurring FXaI was calculated following the classical dose response method. Ki values were obtained by plotting the percentage of activity of FXaI (determined by the calorimetric assay described below) against the ratio of the concentrations of inhibitor and enzyme. The calorimetric assay was performed using 80 µM Chromozyme TH (Pentapharm, Switzerland) as substrate in 10 mM Tris-HCl, 10 mM Hepes (pH 7.8), 100 mM NaCl, 0.1% PEG 6000 at 25° C. in the presence of 3.83 or 4.27 nM bovine trypsin. Inhibitor and enzyme were preincubated for 10 min at 25° C. before adding the substrate. In this assay, the Ki for naturally occurring FXaI was found to be 47.3 nM.

(iii) Inhibition of Plasmin and Thrombin

Plasmin and thrombin were not inhibited by naturally occurring FXaI in a similar assay as that for trypsin. In the case of thrombin, the substrate used was the same as that used for trypsin; in the case of plasmin, S2251 was used as substrate.

7. Pharmacokinetic Study of FXaI

A preliminary pharmacokinetic experiment was performed in order to assess the clearance rate of FXaI from the circulatory system. Female Balb/c mice (20–25 gm body weight) were injected intravenously with purified FXaI (isoform A; 5.25 µg protein/mouse in 0.2 ml saline). Blood samples were drawn into 1/10 v/v 3.8% citrate at 1, 3, 10 and 30 min after injection. It was possible to obtain only one blood sample from each mouse and therefore each timepoint is from a different mouse. The plasma was then separated and assayed for APTT. The concentration of FXaI was calculated from a calibration curve of APTT versus FXaI concentration which was constructed in vitro by adding various amounts of FXaI to a plasma pool from untreated mice FIG. 5B.

The results of the in vivo study are summarized in Table 2 and FIGS. 5A and 5B. The actual APTT values measured at the various time points specified are shown in Table 2. In FIGS. 5A and 5B, these data are expressed in terms of amount of inhibitor present in the sample at each time point. Significant inhibition of blood clotting was obtained immediately after the intravenous administration of FXaI, and the plasma levels of inhibitor activity dropped rapidly, with a half life of about 7.5 min.

TABLE 2

Time dependence of ex vivo APTT following injection of mice with FXaI

| Animal No. | Blood Samples: time post-injection (min) | Mean APTT (sec) | FXaI* (μg) |
|---|---|---|---|
| 1 | 1 | 91 | 0.3150 |
| 2 | 3 | 79 | 0.243 |
| 3 | 3 | 66 | 0.174 |
| 4 | 10 | 55 | 0.1245 |
| 5 | 30 | 29 | 0 |
| 6 | 30 | 30 | 0 |

*Calculated from the calibration curve

EXAMPLE 3

Cloning of FXaI cDNA by PCR

The following procedure is shown schematically in FIG. 7. Total RNA was extracted from 120 leeches. From the total RNA, 35 μg of poly $A^+$ mRNA were isolated (using the Fast Track™ mRNA isolation kit, Invitrogen). An aliquot (5 μg) of the poly $A^+$ mRNA so obtained was used as template in a reverse transcription reaction in the presence of the following synthetic primer:

A: (SEQ. ID NO. 10)
       XhoI      HindIII
5'- AACTCGAGGATCCAAGCTTTTTTTTTTTTTTT -3'
              BamHI The 15-mer oligo-dT sequence provides complementarity to the poly A sequence of the various mRNAs.

Following synthesis of the single stranded complementary DNA (ss-cDNA), the mRNA was degraded by alkali treatment (0.3M NaOH overnight at room temperature). An aliquot of the neutralized ss-cDNA was then subjected to PCR amplification using as reverse primer the following synthetic degenerative DNA oligomer:

B: (SEQ. ID NO. 11)
         NdeI      T  A        T    T  T
5'-CCGAATTCATATGTA GA GTTATTA GTTGA GA CC-3'
    EcoRI          C  G        C    C  C

This synthetic primer was prepared in accordance with the first nine N-terminal amino acids of FXaI (Example 2) and encodes the sequence:

$NH_2$-Tyr-Glu-Val-Ile-Tyr-Val-Asp-Asp-Pro-(COOH). (SEQ. ID NO. 12)

The PCR amplification conditions were as follows:

| 1. | Primer A | 0.2 μg |
|---|---|---|
| 2. | Primer B | 0.2 μg |
| 3. | ss-cDNA | 5 μl (5% of total) |

| 4. | 5 mM dNTP | 4 μl |
|---|---|---|
| 5. | 10X PCR buffer | 10 μl |
| 6. | Taq polymerase | 0.2 μl (8U/μl (USB)) |
| 7. | $H_2O$ | 81 μl |
| 8. | 40 cycles × [1' at 94° C.; 3' at 37° C. and 4' at 72° C.] | |

To analyze the PCR amplification products, 10 μl of the 100 μl reaction were loaded onto a 1% agarose gel. Non-amplified controls and size markers were also included. Three distinct bands of about 350 bp, 450 bp and 700 bp were observed. The three bands were blotted onto nitrocellulose paper and then hybridized to a synthetic radiolabeled DNA probe (probe C) corresponding to N-terminal amino acids 14 to 19 of the $NH_2$-terminal sequence disclosed in Example 2 (section 2.1 above) and having the following sequence:

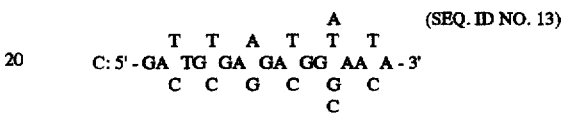

A         (SEQ. ID NO. 13)
           T  T  A  T  T
C: 5'- GA TG GA GA GG AA A -3'
       C  C  G  C  G  C
                    C

The three PCR products were found to hybridize with probe C under hybridization conditions of high stringency. However, the band corresponding to the 700 bp fragment was found to hybridize relatively poorly to the 350 bp and 450 bp fragments.

Following PCR amplification, the DNA was purified from the reaction mixture by chloroform and phenol extractions and ethanol precipitation. The DNA was then digested with EcoRI and HindIII and following gel purification, the fragments were subcloned into the large EcoRI-HindIII fragment of plasmid pSP65 (FIG. 7). The ligation mixture was used to transform E. coli strain MC1061. Transformants were screened by in-situ hybridization using the radiolabeled synthetic probe C disclosed above.

Plasmid DNA was prepared from positive clones. Those plasmids containing an EcoRI and HindIII fragment of the expected size were subjected to DNA sequencing using the Sanger dideoxy sequencing method. In this fashion two classes of clones were obtained: (A) those with an insert of about 290 bp (clones 3, 8 and 12) and (B) those with an insert of about 450 bp (clones 1, 4, 5 and 16). The plasmids of clones 3 and 4 were designated pSP65-XaI-3 and pSP65-XaI-4 respectively.

The DNA sequence and deduced amino acid sequence of clone pSP65-XaI-4 (clone 4) is shown in FIG. 8. It is noted that $met^5$ in FIG. 8 is the fourth amino acid ($met^1$ is the initiator methionine added by the bacterial host cell) of the FXaI polypeptide which differs from $ile^4$ which is the fourth amino acid of the N-terminal sequence noted above. This discrepancy is apparently due to a mistake by the DNA polymerase in the course of the PCR reaction.

In vitro translation using wheat germ lysate showed that clone 4 encodes a protein of the same size as clone 3. It might therefore be that the shorter nucleotide sequence (290 bp) of clone 3 is due to internal priming by a poly-A rich sequence at the 3' non-translating region of the mRNA encoded by DNA exemplified by the 450 bp nucleotide sequence of clone 4 which was used as template in the reverse transcription reaction described at the beginning of this Example.

EXAMPLE 4

Isolation and Cloning of DNA Encoding FXaI From a Hirudo medicinalis cDNA Library The PCR derived cDNA disclosed in Example 3 (clones 3 and 4) was isolated by hybridization with a probe corresponding to the N-terminal sequence of the purified naturally occurring protein. In order to provide further confirmation and verification of the PCR derived sequence, a cDNA library of Hirudo medicinalis was constructed. The resulting clones were screened using as DNA probe the entire FXaI coding sequence of clone 4. The procedure is shown schematically in FIG. 9.

Total RNA was extracted from 120 leeches. Poly A⁺ mRNA was isolated from total RNA using the Fast Track™ mRNA isolation kit. An aliquot of the poly A⁺ mRNA so obtained was used for ds-cDNA (double stranded cDNA) synthesis using the ZAP™ cDNA synthesis kit (Stratagene).

The resulting ds-cDNA was digested with XhoI and EcoRI and subcloned into the XhoI and EcoRI digested Uni-ZAP™ phagemid vector (Stratagene). Upon plating of the resulting recombinant phage on E. coli XL1-Blue™ (Stratagene), a cDNA library of about $1.5 \times 10^5$ plaques was obtained (FIG. 9).

This cDNA library was screened for clones containing FXaI DNA using as probe radiolabeled DNA from the PCR derived plasmid, pSP65-XaI-4 (Example 3) under hybridization conditions of both low and high stringency.

Conditions of high stringency included prehybridization of the filter for 8 hours at 60° C. in 6× SSC (1× SSC: 0.15M NaCl, 0.015M Na-citrate), 0.1% SDS, 5× Denhardt (0.1% Ficoll 400, 0.1% polyvinyl pyrrolidone, 0.1% BSA, 0.5% SDS) and 100 µg/ml salmon sperm DNA, followed by hybridization with the radioactive probe for 48 hours at 60° C. Filters were washed with 2× SSC-0.2% SDS for 2 hours at 60° C. several times before autoradiography.

Positive plaques were picked, isolated and rescreened under the same hybridization conditions. Plasmids of several positive clones were then recovered with the aid of helper phage and sequenced by the Sanger dideoxy method.

The plasmid of one of the clones was designated pSK-XaI-11 (herein "clone 11" or "11") and selected for further manipulation and analysis. Several other cDNA clones were also sequenced, but all were truncated at the 5' end or had a different sequence.

Clone 11 contains a 684 bp DNA insert (FIG. 10) which was found to be essentially identical to the previously obtained PCR derived sequences, however containing 78 additional base pairs at its 5' end. This additional sequence encodes a peptide having 13 hydrophobic and 2 positively charged residues which is a composition typical of leader peptides.

We have analyzed the N-terminal amino acid sequence of the product of clone 11 for the presence of a putative leader sequence. The analysis was carried out using the algorithm of Von Heijne (Nucleic Acids Res. 14: 4683–91, 1986). This algorithm predicts the probability of a given amino acid to occupy a certain position within a leader sequence and thus can determine whether the peptide sequence conforms with that of a leader sequence. Moreover, by determining the "combined amino acid score" along the peptide, the cleavage site between the leader sequence and the mature protein can also be predicted. When applied to the analysis of the N-terminal sequence of the product of plasmid pSP65-XaI-11 (FIG. 10), this algorithm identified a pattern of amino acids, beginning with $met^1$ and continuing through $ser^{25}$, consistent with that of a leader peptide and the cleavage site was found between $ser^{25}$ and $tyr^{26}$. Based on the above analysis, the sequence depicted in FIG. 10 encodes a prepeptide: from $met^1$ through $ser^{25}$ the sequence encodes a leader peptide and from $tyr^{26}$ through $glu^{110}$, the sequence encodes a mature protein identical to the naturally-occurring FXaI.

Accordingly, the DNA of clone 11 codes for a prepeptide of 110 amino acids (including N-terminal methionine) extending from $met^1$ through $gly^{110}$ (FIG. 10) containing 15 cysteine residues, one of which is located in the 25 amino acid signal or leader peptide. As described in the preceding paragraph, amino acids 1 through 25 of clone 11 apparently constitute a leader sequence. This finding is further supported by the fact that the known N-terminal sequence determined for the naturally occurring protein isolated from DLS begins at $tyr^{26}$ (Example 2). It is therefore reasonable to assume that the mature protein encoded by clone 11 (recombinant FXaI) comprises 85 amino acids extending from $tyr^{26}$ through $gly^{110}$.

In order to confirm the existence of an open reading frame in the cloned cDNA and to verify the size of the encoded protein, the cDNA insert was cloned into plasmid SP65 and SP6 RNA was prepared using the Stratagene in vitro translation kit. The RNA thus obtained was subjected to in vitro translation and the protein products were analyzed on SDS-PAGE under denaturing conditions.

The protein product of in vitro translation of mRNA encoded by clone 11 migrated on the gel at a position corresponding to about 15 kD.

As previously described, clone 4 was isolated on the basis of the N-terminal sequence of the naturally occurring polypeptide and is therefore considered to encode the naturally occurring polypeptide. Clone 11 was isolated on the basis of the nucleotide sequence of clone 4. The deduced amino acid sequence of clone 4 is shown in FIG. 8, and that of clone 11 in FIG. 10. The amino acid sequences of clones 4 and 11 are also shown aligned in FIG. 6.

The sequence $tyr^2$-$gly^{86}$ of clone 4 (FIG. 8) is equivalent to the sequence $tyr^{26}$-$gly^{110}$ of clone 11 (FIG. 10). Comparison of the two sequences reveals that there are only two differences between them. $Met^5$ of clone 4 is parallel to $ile^{29}$ of clone 11, and $ser^{65}$ is parallel to $pro^{89}$ of clone 11. $Met^5$ of clone 4 was apparently inserted by mistake by the PCR reaction instead of isoleucine which is the corresponding residue in the N-terminal sequence obtained from naturally occurring polypeptide isolated from DLS. These differences may also be more clearly observed in FIG. 6 at positions 4 and 70. Therefore, there is at most only one difference between the polypeptide encoded by clone 11 and the naturally occurring polypeptide, and they therefore may be considered homologs. Accordingly, the polypeptide expressed by clone 11 will be referred to as recombinant FXaI.

EXAMPLE 5

Comparison of Deduced Amino Acid Sequences

The deduced amino acid sequences of PCR derived FXaI cDNA, library derived FXaI DNA (including the leader sequence) and antistasin were compared in different fashions, i.e. by maximum homology, identical homology, and alignment.

5.1 Homology

The degree of maximum homology (expressed as per cent in Table 3) was found using the 2020 PROSIS program (LKB), Version 6.00 which is based on Needleman and Wunsch, J. Mol. Biol. 48:443 (1970) using the equivalence groups noted in the footnote to the Table 3. The sequences compared included the leader peptides.

TABLE 3

| | Degree of maximum homology* | | |
|---|---|---|---|
| Clone | Antistasin | Clone 4 | Clone 11 |
| Antistasin | 100 | 50 | 45 |
| Clone 4 | 50 | 100 | 78 |
| Clone 11 | 45 | 78 | 100 |

*The maximum homology program uses the following equivalence groups:
(1) A, S, T, P, G
(2) N, D, E, Q
(3) H, R, K
(4) M, L, I, V
(5) F, W, Y Table 4 shows the degree of identical homology (expressed in per cent), i.e. without equivalence groups.

TABLE 4

| | Degree of identical homology* | | |
|---|---|---|---|
| Clone | Antistasin | Clone 4 | Clone 11 |
| Antistasin | 100 | 32 | 30 |
| Clone 4 | 32 | 100 | 77 |
| Clone 11 | 30 | 77 | 100 |

*Homology without equivalence groups

5.2. Alignment

Another way to analyze the similarity of sequences is to align the cysteine residues, even at the expense of homology. The computer program Pileup based on the work of Feng and Doolittle, J. Mol. Evol. 35:351–360 (1987) performs such alignment. The result, utilizing the parameters of gap weight 3.00 and gap length weight 0.10, for the same sequences compared above, is shown in FIG. 6. FIG. 6 shows that 14 of the cysteines of all 3 sequences can be aligned without introducing considerable gaps in any of the sequences. The Pileup program assigns a value on a scale of 0–1.5 expressing the degree of similarity of sequences. The resulting degree of similarity of the present sequences is shown in Table 5 as a percent of 1.5.

TABLE 5

| | Index of similarity | | |
|---|---|---|---|
| Clone | Clone 4 | Clone 11 | Antistasin |
| Clone 4 | 100 | 100 | 41 |
| Clone 11 | 100 | 100 | 32 |
| Antistasin | 41 | 32 | 100 |

From these three methods of comparing amino acid sequences, it is seen that there is only little similarity between antistasin and clones 4 and 11. Antistasin shows only 50% and 45% maximum homology with clones 4 and 11 respectively; only 32% and 30% identical homology with clones 4 and 11 respectively; and index of similarity to clones 4 and 11 of 41% and 32% respectively.

EXAMPLE 6

Expression of Recombinant FXaI

In order to obtain plasmids for the expression of recombinant FXaI in *E. coli*, further manipulation of the DNA fragments coding for the FXaI proteins was required. Plasmid pSK-XaI-11 (Example 4) was digested with XhoI and EcoRI. The XhoI-EcoRI fragment containing the FXaI-encoding sequence was isolated and subcloned into a SalI-EcoRI digest of plasmid pSP65. The resulting plasmid was designated pSP65-XaI-11 (FIG. 11). This plasmid lacks suitable regulatory elements and therefore does not express the encoded protein; however, it may be used in the construction of expression plasmids.

Bacterial expression of recombinant FXaI encoded by clone 11 was obtained by using cDNA fragments to construct a plasmid for expression of FXaI fused to 63 N-terminal amino acids of human Cu/Zn-SOD.

Plasmid pSP65-XaI-11 containing the cDNA of clone 11 was digested with RsaI. The RsaI-RsaI fragment coding for FXaI was isolated and ligated to the large AatII-PpuMI fragment of plasmid pBAST-R in the presence of the following two sets of synthetic oligomers:

$^{63}$Pro Met Phe Val
E: 5'- GTCCTATGTTTGTAT -3' (SEQ. ID NO. 14)
F: 3'-      GATACAAACATA -5' (SEQ. ID NO. 15)

HindIII
G: 5'- CGAATTCAAGCTT -3' (SEQ ID. NO. 16)
H: 3'-TGCAGCTTAAGTTCGAA -5' (SEQ ID NO. 17)

The resulting plasmid was designated pDeo-S-XaI-11"f" (FIG. 12) and was deposited in *E. coli* strain 733 under ATCC Accession No 69136.

Plasmid pBAST-R contains the deo $P_1P_2$ promoter, the deo RBS and the N-terminal region of a modified Cu/Zn-SOD sequence. The three additional amino acids met-phe-val encoded by synthetic linker E which are present between the SOD moiety and the FXaI moiety constitute a cyanogen bromide cleavage site.

Thus, plasmid pDeo-S-XaI-11"f" encodes a fusion protein having a molecular weight of about 19 kD containing 63 N-terminal amino acids of a modified Cu/Zn-SOD sequence, a cleavage or linker region between the two fused proteins consisting of the tripeptide met-phe-val encoded by linker E, and FXaI having the sequence tyr$^{26}$ to gly$^{110}$ shown in FIG. 10.

The modified SOD moiety has the amino acid sequence
MET ALA THR LYS ALA ALA SER VAL LEU LYS GLY ASP GLY PRO VAL GLN GLY ILE ILE ASN PHE GLU GLN LYS GLU SER ASP GLY PRO VAL LYS VAL TRP GLY SER ILE LYS GLY LEU THR GLU GLY LEU HIS GLY PHE HIS VAL HIS GLU PHE GLY ASP ASN THR ALA GLY SER THR SER ALA GLY PRO. (SEQ. ID NO. 18)

A protein of the expected size was obtained in the insoluble fraction obtained after lysis of the cell pellet following growth of *E. coli* 733 transformed with plasmid pDeo-S-XaI-11"f". Mature FXaI may be obtained by cleavage of the fusion protein by known methods.

EXAMPLE 7

Refolding and Purification of Recombinant FXaI Produced by Plasmid pDeo-S-XaI-11"f"

*E. coli* 733 containing plasmid pDeo-S-XaI-11"f" was grown according to procedures known in the art such as are described in coassigned European Patent Application Publication No. 303,972, Feb. 22, 1989 which discloses methods relating to expression plasmids under control of the deo promoter. Following growth, the cells were pelleted and the cake stored frozen until processing. The processing of the bacterial cakes and the refolding of the recombinant FXaI polypeptide are detailed below.

1. Isolation of Inclusion Bodies

The bacterial cake was suspended in 10 volumes of buffer 1 (50 mM Tris-HCl pH 8 containing 10 mM EDTA). Cell disruption was performed by adding lysozyme (2500 U/ml) to the suspension and incubating with occasional stirring for 2 hours at room temperature. The suspension was then sonicated (3×10 min), followed by centrifugation (12,000 rpm) for 30 min at 4° C. The pellet was washed with detergent by resuspension in 10 volumes of buffer 1 containing 1% Nonidet P-40 (NP-40) and incubated with occasional stirring for 1 hour at room temperature. The suspension was then clarified by centrifugation (12,000 rpm) for 30 min at 4° C. and the pellet further washed with distilled water and incubated with occasional stirring for 15 min at room temperature. The washing of the pellet resulted in removal of much of the E. coli proteins. Finally, the washed pellet was centrifuged (15,000 rpm) for 45 min at 4° C. It was established by SDS-PAGE that the recombinant FXaI fusion protein remained in the pellet under the conditions of washing.

2. Solubilization and Reduction

Most of the recombinant FXaI appeared in inclusion bodies, i.e., in the insoluble pellet obtained following sonication of the bacteria. Following isolation and washing, the inclusion bodies were solubilized in 48 volumes of 6M guanidinium chloride (GuCl) in buffer 2 (20 mM Tris-HCl pH 8 containing 1 mM EDTA and 100 mM NaCl). Reduction was initiated after 15 min by the addition of 10 mM reduced glutathione (GSH) under a stream of nitrogen and was allowed to proceed for 1 hour. The protein concentration was then adjusted to 1 mg/ml by the addition of GSH-containing buffer 2 and further incubated for 1-3 hrs under nitrogen.

3. Refolding/Reoxidation

The crude mixture so obtained containing reduced recombinant FXaI was diluted up to ten-fold in buffer 2 (final GuCl and GSH concentrations 0.6M and 1 mM, respectively) to a protein concentration of 100 µg/ml protein. Oxidized glutathione (GSSG) was added to a final concentration of 0.1 mM and the solution was incubated for 16 h at 4° C. The oxidized protein was dialyzed with 3 buffer changes against buffer 2 lacking EDTA, before assaying its inhibitory activity in the chromogenic assay.

4. Inhibitory Activity of Various Batches of Refolded Recombinant FXaI

The refolded and dialyzed protein so obtained was assayed for FXa inhibitory activity by the biochemical chromogenic assay described in Example 2. The results are shown in Table 6 as milliunits per mg protein (mu/mg). The amount of protein causing 50% inhibition in an assay mixture containing 2 nM FXa is defined as 1 mu. In addition, the refolded protein was also tested for its inhibitory effect on thrombin, another proteolytic enzyme of the coagulation cascade, which was assayed according to Lottenberg et al. Methods Enzymol. 80:341-361 (1981). As seen from Table 6, no significant level of inhibition of thrombin by FXaI was observed (<1 mu/mg).

TABLE 6

Inhibitory Activity* of FXaI Fusion Protein

| FXaI → | Naturally Occurring FXaI[a] | Refolded 11"f" | | |
|---|---|---|---|---|
| | | Batch 1 | Batch 2 | Batch 3[b] |
| Enzyme ↓ | | | | |
| FXa | 507 | 150 | 95 | 89 |
| Thrombin | <1 | nd[c] | nd | <1 |

*Specific activity, mu/mg
[a]Isoform B isolated from DLS
[b]Further purified on Q- and Heparin-Sepharose
[c]nd - not determined In summary, biologically active recombinant FXaI has been produced by refolding the FXaI fusion protein produced by clone 11"f". The recombinant protein so obtained has specific activity in the same range as that of naturally occurring FXaI isolated from DLS.

The recombinant protein shows a specificity for FXa which is greater than 80 fold higher than for thrombin.

EXAMPLE 8

Elicitation of Antibodies Against FXaI

Antibodies were raised against naturally occurring FXaI isolated from DLS.

A. Preparation of Antigen

Antigen for immunization was purified from DLS by Q-Sepharose and Heparin-Sepharose chromatography as described in Example 1. An aliquot of the protein was diluted with an equal volume of SDS-PAGE sample buffer (30% glycerol, 0.19M Tris-HCl pH 6.8, 10% SDS, 15% β-mercaptoethanol, and 0.004% bromphenol blue). The sample was then electrophoresed on a 15% SDS-PAGE gel, electro-transferred onto a nitrocellulose membrane, and stained with reversible Ponceau stain. Protein having an apparent molecular molecular weight of about 14 kD was extracted from the membrane, and used as antigen for immunization.

B. Elicitation of Antibodies

Purified antigen (20–60 μg) dissolved in 1 ml DMSO and mixed with complete Freund's adjuvant, was injected into the foot pads of a 1.8–2.3 kg rabbit. After 3 weeks, the rabbit was again injected, this time subcutaneously with the same amount of antigen mixed with incomplete Freund's adjuvant. This procedure was repeated twice more at the same interval.

C. Antibody Verification by Western Blot Analysis

Antibodies were verified on a Western blot of various proteins run on a 12% SDS-PAGE run under reducing conditions. Following reaction with the antisera, the Western blots were developed with $^{125}$I-labeled protein A.

D. Results

Anti-FXaI reacted both with the naturally occurring FXaI purified from DLS, and with the refolded and partially purified recombinant FXaI fusion peptide produced by clone 11"f". The naturally occurring FXaI and the recombinant FXaI fusion peptide (11"f") migrated on the gel with molecular weights of 16 kD and 23 kD respectively. The bands obtained on a Western blot of the same proteins following reaction with anti-FXaI had identical molecular weights, clearly showing that recombinant FXaI cross-reacts with naturally occurring FXaI.

EXAMPLE 9

Production of Recombinant FXaI in Eukaryotic Cells

Due to the inherent complexity of refolding a molecule containing many cysteines, such as FXaI, to obtain a biologically active polypeptide, it is postulated that production of the polypeptide in eukaryotic cells might eliminate some of the difficulties. It is envisioned that this may enable production of large amounts of properly refolded, biologically active recombinant protein.

In preliminary experiments, expression of the mature FXaI polypeptide was obtained using a baculovirus expression system in Sf-9 insect cells (18). The cells had been transformed with DNA encoding the 11"I" protein, i.e. DNA encoding the FXaI prepeptide including its leader sequence (as contained in plasmid pSK-XaI-11 (FIG. 9)).

Western blot analysis showed that the resulting polypeptide which was secreted into the medium, had undergone post-translational processing in the host cell, i.e. removal of the leader sequence, thus enabling recovery of refolded, biologically active mature FXaI polypeptide.

The polypeptide produced reacted with the anti-FXaI antibodies described in Example 8.

EXAMPLE 10

Additional Plasmids Expressing Recombinant FXaI and Prepeptides

In order to obtain improved expression of recombinant FXaI in *E. coli*, additional manipulations of the DNA fragment coding for FXaI were required.

A series of plasmids comprising DNA encoding FXaI and comprising the following combinations of different regulatory elements were constructed which did not result in detectable expression of FXaI or resulted in expression of FXaI detectable only by Western Blot analysis:

(a) $\lambda P_L$ promoter, $\lambda C_{II}$ ribosomal binding site and eight His residues after the ATG codon.

(b) $\lambda P_L$ promoter, modified $\lambda C_{II}$ ribosomal binding site (9 nucleotides instead of 12) and a leader sequence similar to the DsbA leader sequence (19) in an attempt to secrete the expressed protein into the bacterial periplasm.

(c) $\lambda P_L$ promoter, modified $\lambda C_{II}$ ribosomal binding site (9 nucleotides), a leader sequence similar to the DsbA leader sequence in an attempt to secrete the expressed protein into the bacterial periplasm, a $T_1T_2$ transcription termination sequence and the $cI^{857}$ repressor.

(d) deo promoter, deo ribosomal binding site, translation enhancer and a leader sequence similar to the DsbA leader sequence.

(e) $\lambda P_L$ promoter, deo ribosomal binding site, translation enhancer, a leader sequence similar to the DsbA leader sequence in an attempt to secrete the expressed protein into the bacterial periplasm, a $T_1T_2$ transcription termination sequence and the $cI^{857}$ repressor.

Two plasmids comprising DNA encoding FXaI and comprising combinations of different regulatory elements were constructed which did result in detectable expression of FXaI:

I. Plasmid pFSHI-6

A series of plasmids was constructed culminating in plasmid pFSHI-6 (FIG. 13), which upon transformation of the proper *E. coli* host cells was capable of directing expression of FXaI attached to an extension peptide (a FXaI prepeptide) comprising 14 amino acids (one Met residue, 6 His residues, one Gly residue, one Thr residue and the amino acids required for an endoproteinase cleavage site, i.e. Asp-Asp-Asp-Asp-Lys which are recognized by enterokinase) useful for FXaI production.

Figure 13:
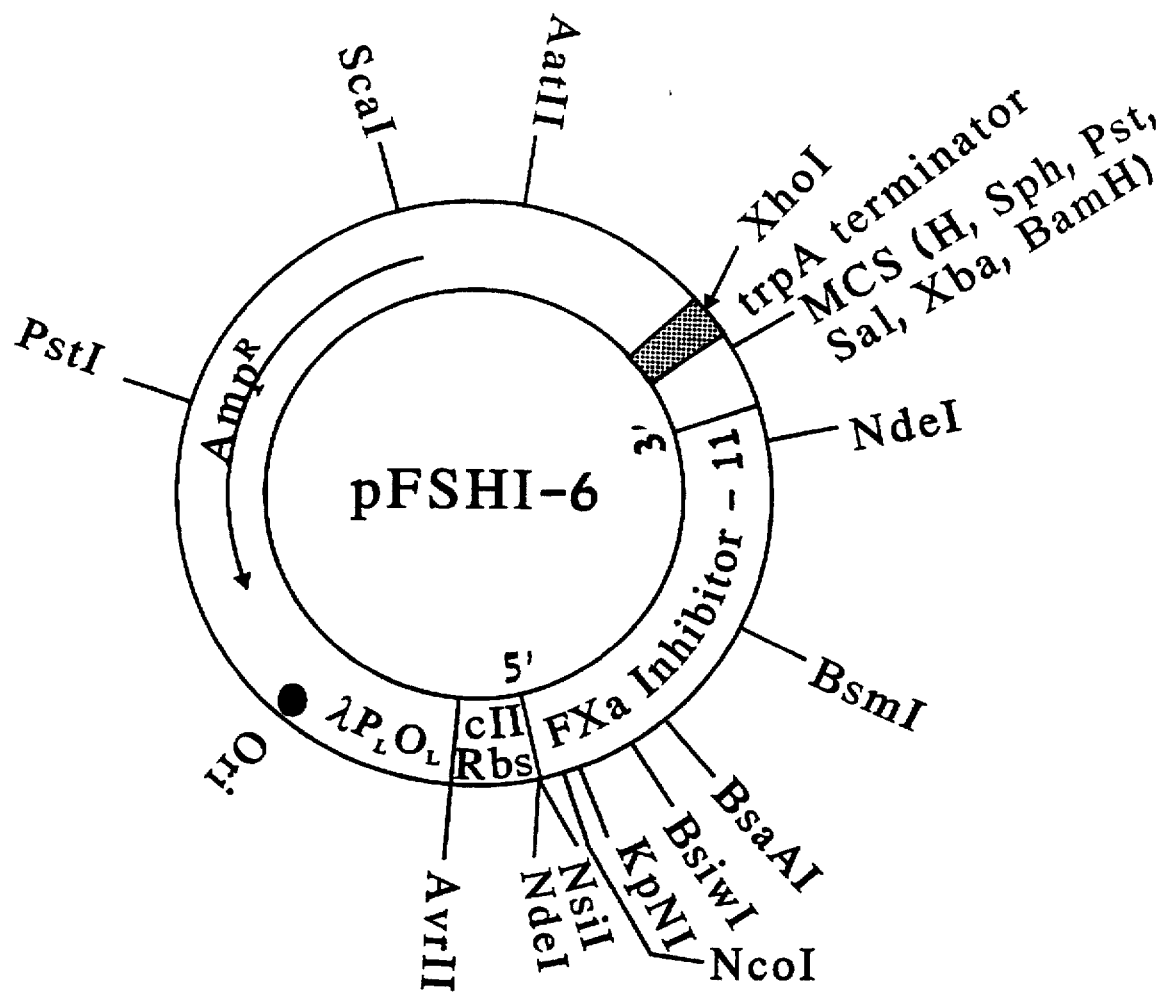

The structure of plasmid pFSHI-6, encoding Met-His-His-His-His-His-His-Gly-Thr-Asp-Asp-Asp-Asp-Lys-FXaI (SEQ. ID NO. 19) is shown in FIG. 13. The amino acid sequence of FXaI is shown in FIG. 10 and starts from amino acid Tyr at position 26.

Plasmid pFSHI-6, which confers ampicillin resistance and which encodes Met-His-His-His-His-His-His-Gly-Thr-Asp-Asp-Asp-Asp-Lys-FXaI, (SEQ. ID NO. 20) was introduced into *E. coli* strain 4300 and deposited in the ATCC under ATCC Accession No. 69583 on Mar. 11, 1994.

The host-plasmid system was grown in LB medium supplemented with 100 μ/ml ampicillin until $O.D._{660}=0.8$. Production of the protein was induced upon temperature shift to 42° C. for 15 minutes. The temperature was then lowered to 40° C. and the system further cultured for 2 hours.

SDS-PAGE analysis and Western blot analysis revealed a new protein band of about 17 kDa, not present in control culture harboring no plasmid.

To determine the localization of the FXaI in the cell extract, the induced culture was harvested, washed with 50 mM Tris-HCl, pH 8.0, 10 mM EDTA and sonicated to disrupt the cells. After centrifugation at 15,000 rpm (Sorvall centrifuge), the supernatant was separated from the pellet. The pellet was suspended in 8M urea to solubilize particles and membranes. SDS-PAGE analysis of both fractions revealed that the FXaI expressed was present in the supernatant, i.e. was in soluble form.

The polypeptide expressed by plasmid pFSHI-6 in soluble form was isolated by the following procedure: induced culture from 1 liter media was harvested, suspended in 50 mM Tris-HCl, pH 8.0, 10 mM EDTA, 20 μg/ml lysozyme in a final volume of 50 ml. Following cell disruption, the supernatant was diluted 1:1 with $H_2O$ and loaded onto a DEAE-Sepharose column equilibrated with 25 mM Tris-HCl, pH 8.0 (this can alternatively be done using a Q-Sepharose column). The protein was eluted with a 0–0.5M NaCl gradient in the same buffer. The fraction containing the 17 kDa protein was pooled and the pH adjusted to 6.8 with acetic acid. Metal affinity column chromatography (Invitrogen) was carried out by equilibrating the $Ni^{++}$ column with 0.3–0.5M NaCl in 25 mM Tris-HCl, pH 8.0. The protein was loaded onto the column (3 ml bed volume) washed with the same buffer and the bound FXaI eluted with 0.3M imidazole in the same buffer. The pooled fractions were dialyzed against 50 mM Tris-HCl, pH 8.0. SDS-PAGE analysis revealed that the 17 kDa protein band was the predominant protein expressed. Protein purity was estimated to be about 70–80%.

The partially purified protein was subjected to cleavage in 20 mM NaPi buffer, 100 mM NaCl, 0.1% of the detergent Hecameg™ (Vegatec, Ville-Juife, France), pH 6.6 with Enterokinase (Biozyme, Great Britain) at 37° C. for 40 hours. Protein to enterokinase ratio was 200 μg:1 μg respectively. The cleavage efficiency was 95% as determined by SDS-PAGE analysis. The 17 kDa protein band was converted to a new protein band corresponding to a molecular weight of about 15 kD as visualized by Coomassie Blue staining. After cleavage, the cleaved protein was dialyzed against 20 mM NaPi, 100 mM NaCl, pH 6.6 to remove detergent and the cleaved extension peptide.

The FXa inhibitory specific activity was assayed in a chromogenic assay (as described in Example 2) prior to and following cleavage with enterokinase. The specific activity prior to cleavage was 1000–1200 mu/mg protein and following cleavage it was 4000–4500 mu/mg protein. The specific activity was as high as 8000 mu/mg protein after removal of the extension peptide from the cleavage solution by chromatography.

N-terminal amino acid sequencing performed on the cleaved protein confirmed that the first nine (9) amino acids of the cleaved protein are identical to the first nine amino acids of FXaI as shown in FIG. 10 (from Tyr$^{26}$ to Pro$^{34}$).

The concentration of mature FXaI causing doubling of the APTT was 12.2 µg/ml.

II. Plasmid pFSOH-11

In order to be able to use hydroxylamine (instead of enterokinase) for obtaining mature FXaI, the DNA sequence encoding the FXaI present in plasmid PFSHI-6 was manipulated by introducing two additional triplets, coding for Asn-Gly, after the Lys residue in the extension peptide (the C-terminal residue of the extension peptide). Concomitantly, the Asn residue at position 47 of FXaI (position 72 in FIG. 10) was replaced with a Pro residue to remove a hydroxylamine sensitive site within the FXaI coding region.

Furthermore, the following nucleotide changes, which do not affect the amino acid sequence of FXaI, were made (in comparison to the nucleotide sequence depicted in FIG. 10):

| | | |
|---|---|---|
| $G^{223} \rightarrow A$ | $A^{319} \rightarrow C$ | $T^{381} \rightarrow G$ |
| $A^{226} \rightarrow C$ | $A^{321} \rightarrow T$ | $T^{427} \rightarrow C$ |
| $G^{232} \rightarrow C$ | $A^{349} \rightarrow T$ | $A^{432} \rightarrow T$ |
| $A^{252} \rightarrow T$ | $G^{350} \rightarrow C$ | $A^{459} \rightarrow C$ |
| $A^{277} \rightarrow T$ | $T^{351} \rightarrow C$ | $A^{460} \rightarrow C$ |
| $G^{278} \rightarrow C$ | $A^{366} \rightarrow T$ | $A^{462} \rightarrow T$ |

Figure 14:
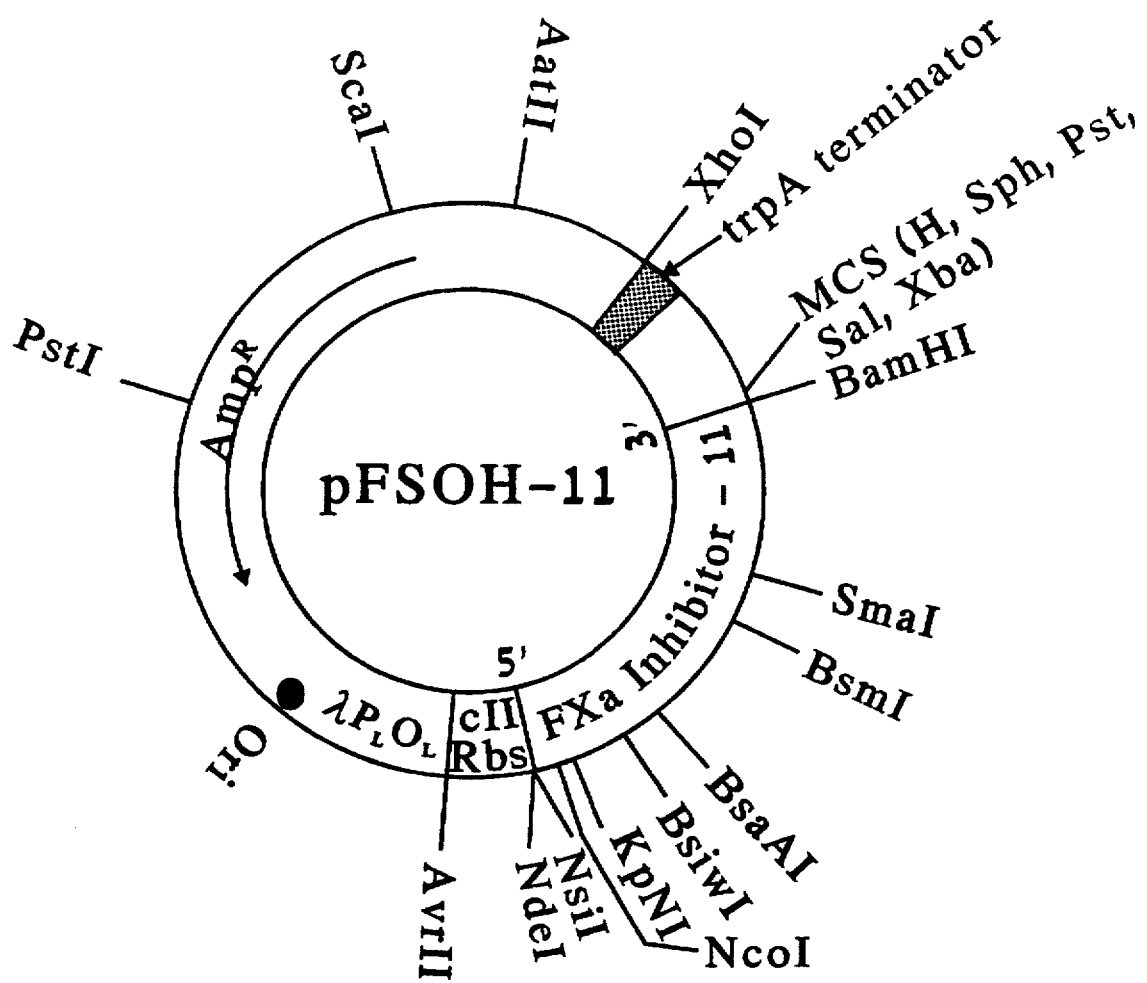

The resulting plasmid was designated plasmid pFSOH-11 (FIG. 14). The newly introduced Asn-Gly site can be cleaved by hydroxylamine yielding mature FXaI starting with Gly-Tyr$^1$-Glu$^2$.

Plasmid pFSOH-11 which confers ampicillin resistance and which encodes Met-His-His-His-His-His-His-Gly-Thr-Asp-Asp-Asp-Asp-Lys-Asn-Gly-FXaI, (SEQ. ID NO. 21) was introduced into E. coli strain 4300 and deposited in the ATCC under ATCC Accession No. 69582 on Mar. 11, 1994.

The host-plasmid system was grown in LB medium supplemented with 100 µ/ml ampicillin until O.D.$_{600}$=0.8. Production of the protein was induced upon temperature shift to 42° C. for 15 minutes. The temperature was then lowered to 40° C. and the system was further cultured for 90 minutes.

SDS-PAGE analysis revealed a new 14–16 kDa protein band, not present in a control culture.

EXAMPLE 11

Expression of an FXaI Dimer Protein

A series of plasmids was constructed culminating in plasmid pMLK-XaI-D-11"m" (FIG. 15), which upon transformation of the proper E. coli host cells was capable of directing expression of an FXaI dimer protein useful for mature FXaI production.

In order to avoid mutation (or deletion) due to self-complemetarity, a DNA fragment encoding FXaI was constructed by assembly of synthetic oligonucleotides using alternative codons to those present in the FXaI fragment prepared by cDNA synthesis (Example 4). The synthetic FXaI fragment was designated FXaI-11"m"-Sy whereas the FXaI fragment prepared as described in Example 4 was designated FXaI-11"m" (FIG. 15).

Figure 15:
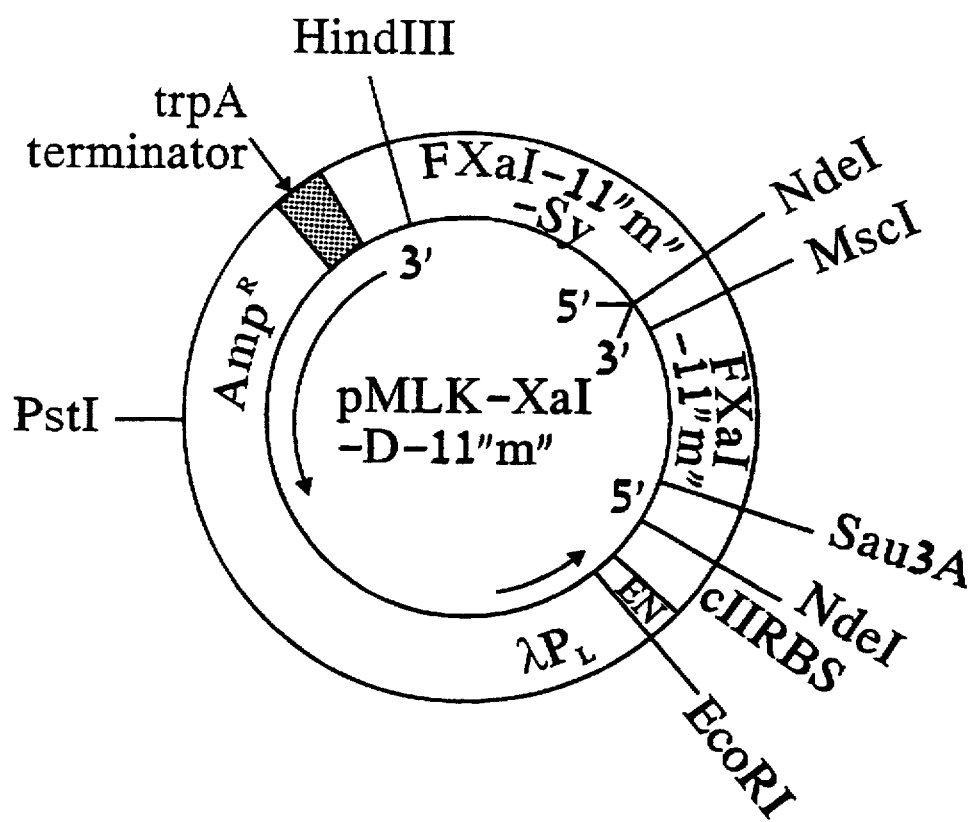

The structure of plasmid pMLK-XaI-D-11"m" encoding an FXaI dimer is shown in FIG. 15.

Plasmid pMLK-XaI-D-11"m" which confers ampicillin resistance and which encodes an FXaI dimer was introduced into E. coli strain 4300 and deposited in the ATCC under ATCC Accession No. 69591 on Mar. 22, 1994.

Plasmid pMLK-XaI-D-11"m" was used to transform E. coli 4300 which contains the thermolabile repressor cI$^{857}$. Upon induction at 42° C., the transformed cells were found to express a polypeptide having a molecular weight of about 28 kD, not present in control culture. The 28 kD polypeptide was obtained from the insoluble fraction obtained after lysis of the cell pellet. The 28 kD protein was the major protein in the cell extract of the recombinant bacteria, as was visualized by Coomassie Brilliant Blue staining. The dimer is cleaved by cyanogen bromide (CNBr) to yield mature FXaI (see Example 12).

EXAMPLE 12

Recovering Active Recombinant FXaI from Inclusion Bodies Containing an FXaI Dimer Plasmid pMLK-XaI-D-11"m" (FIG. 15) encodes a dimeric version of FXaI (Example 11). There are two routes of recovering active FXaI from this dimer:

I. cleaving the dimer with CNBr and then refolding the resulting molecule.

II. refolding the dimer and then cleaving the dimer with cyanogen bromide (CNBr);

Route I

A. CNBr cleavage

The wet inclusion bodies (IB)—0.3 g—were dissolved in 10 volumes of 6M guanidinium chloride—GuCl, 100 mM Tris.HCl (pH 8.5), stirred for 1 h, diluted 1:10 in water and centrifuged (Sorvall, 12,000 rpm, 30 min). The pellet was washed in water, centrifuged (Sorvall Hi-speed centrifuge, 12,000 rpm, 30 min) and dissolved (sonication was used to achieve an homogeneous solution) at a protein concentration of 10 mg/ml in 6 ml of 85% formic acid; 100 mol CNBr/mol Met residue, i.e., 400 mol CNBr/mol protein, were added under the hood. Following overnight incubation at room temperature, the formic acid was evaporated in a Rotovap, the dried protein was washed 5 times with methanol and evaporated again. The residue was dissolved in water and lyophilized.

B. Refolding

The cleaved protein (23 mg by weight) was dissolved in 2.3 ml (100 volumes) of 6M GuCl in 20 mM Tris-HCl (pH 8), 50 mM NaCl, 1 mM EDTA (buffer TNE); 40 mM GSH was added and the pH adjusted to 8.0. Following overnight incubation, supplementation with 10 mM GSH, additional incubation (1 h) and dilution 1:2.5 in TNE/6M GuCl, the solution was further diluted 1:20 in 0.2 mM GSSG (GSH final concentration 1 mM) in buffer TNE in order to initiate refolding/reoxidation. Incubation at 4° C. took place during 66 hours, and after final dialysis against 20 mM Tris-HCl, pH 8.0, the resulting mature FXaI (75 µg/ml) was tested for FXa inhibitory activity. In parallel, samples were concentrated by vacuum evaporation (Speed-Vac concentration, Savant) for SDS-PAGE analysis.

C. Results

According to SDS-PAGE under reducing conditions, cleavage efficiency was more than 70% and the band of about 28 kD representing the dimer was cleaved into two, yielding a single band of about 14 kD. The other impurities amounted to <10% of the total protein on the gel. When the resulting cleaved, refolded product was tested for specific FXa inhibitory activity in the chromogenic assay (as described in Example 2) its activity was determined to be 1900 mU/mg.

N-terminal amino acid sequencing was performed on the cleaved dimer following refolding and confirmed that the first 5 amino acids of the cleaved product are identical to the first 5 amino acids of FXaI (from $Tyr^{26}$ to $Tyr^{30}$ as depicted in FIG. 10).

Route II

A. Refolding

The wet inclusion bodies (100 mg by weight) were solubilized in 3 ml (30 volumes) of 6M GuCl (buffer TNE). For reduction, 20 mM GSH was added and the pH adjusted to 8.0. After one hour incubation, refolding/reoxidation was initiated by dilution of 1:167 (A) or 1:100 (B)in 0.2 mM GSSG (final concentrations GSH 1 mM, GuCl 0.6M) in TNE buffer.

Following overnight incubation at 4° C., dialysis against 20 mM Tris-HCl, pH 8.0, 20 mM NaCl, and centrifugation (Sorvall Hi-speed centrifuge, 12,000 rpm, 30 min), the refolded protein was detected in the supernatant. The refolded protein was assayed for FXa inhibitory activity in the chromogenic assay as described in Example 2. The protein concentrations of the refolded FXaI were 15 µg/ml (A) and 32 µg/ml (B); their specific FXa inhibitory activities were 1720 mu/mg (A) and 1575 mu/mg (B).

B. CNBr Cleavage

Both refolded proteins (A and B) were dialyzed against water and lyophilized. 400 mol of CNBr/mol protein were added to 135 µg of A and to 288 µg of B (i.e. 325 µg and 654 µg CNBr, respectively) which were dissolved in 85% formic acid. Following overnight incubation at room temperature, the formic acid was evaporated in a Rotovap; the dried proteins were washed 5 times with methanol and evaporated in a Rotovap again. The residues were dissolved in water and assayed for FXa inhibitory activity in the chromogenic assay as described in Example 2.

C. Results

The specific activity results of FXaI were as follows:

A: 2470 mu/mg; protein concentration of 85 µg/ml

B: 4700 mu/mg; protein concentration of 83 µg/ml

References

1. Tuszynski et al., J. Biol. Chem 262:9718–9723 (1987)
2. EPO Publication No. 263,608, published Apr. 13, 1988, of Gasic et al, assigned to The Contributors to the Pennsylvania Hospital
3. Condra et al., Thromb. Haemostas. 61:437–441 (1989)
4. U.S. Pat. No. 4,832,849, May 23, 1989, of Cardin, assigned to Merril Dow Pharmaceuticals
5. European Patent Application Publication No. 419,099, Vlasuk, et al., Mar. 27, 1991
6. Teitel et al., J. Clin. Invest. 71:1383–1391 (1983)
7. Dunwiddie et al., Thromb. Haemostas. 67:371–376 (1992)
8. Dunwiddie et al., J. Biol. Chem. 264:16694–16699 (1989)
9. Waxman et al., Science 248:593–596 (1990)
10. Neeper et al., J. Biol. Chem. 265:17746- (1990)
11. Jacobs, Thromb. Haemostas. 64:235–238 (1990)
12. Vlasuk et al., Thromb. Haemostas. 65:257–269 (1991)
13. U.S. Pat. No. 5,196,335, issued May 23, 1993, Rigbi et al. assigned to Yissum Research Development Co.
14. Hirsh, Drug Therapy 324:1565–1574 (1991)
15. Gold, N. Eng. J. of Med. 323:1483–1485 (1990)
16. Weitz, et al., J. Clin. Invest. 86:385–391 (1990)
17. Sitko, et al., Circulation 85:805–815 (1992)
18. Neutra, et al., Appl. Microbiol. Biotechnol 37:74–78 (1992)
19. Bardwell et al., Cell 67:581–589 (1991).

What is claimed is:

1. A DNA comprising a nucleotide sequence encoding a polypeptide comprising the amino acid sequence X-tyr$^{26}$-gly$^{110}$ wherein tyr$^{26}$-gly$^{110}$ is identical to the sequence shown in FIG. 10 (SEQ. ID NO. 28) and wherein X is methionine or absent and wherein asn$^{72}$ may be substituted by pro.

2. A plasmid comprising the DNA of claim 1 designated pSP65-XaI-11 and deposited under ATCC Accession No. 69138.

3. An expression plasmid comprising the DNA of claim 1.

4. An expression plasmid of claim 3 designated pDeo-S-XaI-11"f" deposited under ATCC Accession No. 69136.

5. An expression plasmid of claim 3 designated pFSHI-6 deposited under ATCC Accession No. 69583.

6. An expression plasmid of claim 3 designated pFSOH-11 deposited under ATCC Accession No. 69582.

7. An expression plasmid of claim 3 designated pMLK-XaI-D-11"m" deposited under ATCC Accession No. 69591.

8. A host-plasmid system comprising the expression plasmid of claim 3, 4, 5, 6 or 7 in a host cell.

9. A host-plasmid system of claim 8 wherein the host cell is a bacterial cell.

10. A host-plasmid system of claim 9 wherein the bacterial cell is an *E. coli* cell.

11. A method of producing a polypeptide comprising the amino acid sequence $X$-$tyr^{26}$-$gly^{110}$ wherein $tyr^{26}$-$gly^{110}$ is identical to the sequence shown in FIG. 10 (SEQ. ID NO. 28) and wherein X is methionine or absent and wherein $asn^{72}$ may be substituted by pro which comprises transforming a host cell with an expression plasmid encoding the polypeptide, culturing the transformed host cell so that the cell produces the polypeptide encoded by the plasmid, and recovering the polypeptide so produced.

12. A method of claim 11 wherein the host cell is a bacterial host cell and the recovering comprises:

(a) disrupting the cell so as to produce a lysate containing the polypeptide;

(b) treating the lysate so as to obtain inclusion bodies containing the polypeptide;

(c) treating the inclusion bodies so as to obtain the polypeptide in soluble form;

(d) treating the resulting soluble polypeptide so as to form biologically active polypeptide;

(e) recovering the biologically active polypeptide so formed; and (f) purifying the biologically active polypeptide so recovered.

13. A method of claim 12 wherein the treating of step (c) comprises the addition of a denaturant.

14. A method of claim 13 wherein the denaturant is guanidinium chloride or urea.

15. A method of claim 12 wherein the treating of step (d) comprises contacting the polypeptide with a mixture of a thiol-containing compound and a disulfide.

16. A method of claim 15 wherein the thiol containing compound is glutathione, thioredoxin, β-mercaptoethanol, or cysteine and the disulfide is oxidized glutathione, cystine, or the product of air oxidation of mercaptoethanol.

17. A method of claim 12 wherein the purifying of step (f) comprises column chromatography.

18. A method of claim 17 wherein the column chromatography comprises either one or both of Q-Sepharose chromatography and Heparin-Sepharose chromatography.

19. A method of claim 12 wherein the polypeptide of step (a) is a dimer.

20. A method of claim 12 wherein following step (c) the polypeptide is subjected to cleavage.

21. A method of claim 12 wherein following step (d) the polypeptide is subjected to cleavage to produce the biologically active polypeptide.

22. A method of claim 20 or 21 wherein the cleavage comprises CNBr cleavage.

23. A method of producing a polypeptide comprising the amino acid sequence $X$-$tyr^{26}$-$gly^{110}$ wherein $tyr^{26}$-$gly^{110}$ is identical to the sequence shown in FIG. 10 (SEQ. ID NO. 28) and wherein X is methionine or absent and wherein $asn^{72}$ may be substituted by pro which comprises:

(a) culturing a host cell containing a plasmid containing DNA encoding the polypeptide attached to an extension peptide, so that the DNA expressed is a prepeptide;

(b) recovering from the cell the prepeptide so expressed;

(c) subjecting the prepeptide to enzymatic cleavage to produce the polypeptide;

(d) purifying the polypeptide.

24. A method of claim 23 wherein step (b) further comprises:

(i) disrupting the host cell so as to form a suspension comprising cell debris and a protein supernatant solution;

(ii) separating said cell debris from the soluble protein supernatant solution;

(iii) purifying the prepeptide from the supernatant by column chromatography.

25. A method of claim 23 wherein step (c) further comprises cleaving the prepeptide with enterokinase or hydroxylamine.

26. A method of claim 24 wherein step (iii) further comprises DEAE- or Q-Sepharose chromatography.

27. A method of claim 26 wherein the chromatography is followed by metal affinity chromatography and dialysis.

* * * * *

SEQUENCE LISTING ( 1 ) GENERAL INFORMATION:

( i i i ) NUMBER OF SEQUENCES: 28

( 2 ) INFORMATION FOR SEQ ID NO:1:

( i ) SEQUENCE CHARACTERISTICS:
        ( A ) LENGTH: 32 base pairs
        ( B ) TYPE: nucleic acid
        ( C ) STRANDEDNESS: unknown
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

```
AACTCGAGGA  TCCAAGCTTT  TTTTTTTTT  TT                          3 2
```

( 2 ) INFORMATION FOR SEQ ID NO:2:

( i ) SEQUENCE CHARACTERISTICS:
        ( A ) LENGTH: 39 base pairs
        ( B ) TYPE: nucleic acid
        ( C ) STRANDEDNESS: unknown
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:2:

CCGAATTCAT ATGTAYGARG TNATNTAYGT NGAYGAYCC 39

( 2 ) INFORMATION FOR SEQ ID NO:3:

( i ) SEQUENCE CHARACTERISTICS:
        ( A ) LENGTH: 15 base pairs
        ( B ) TYPE: nucleic acid
        ( C ) STRANDEDNESS: unknown
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:3:

GTCCTATGTT TGTAT 15

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: unknown
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:4:

ATACAAACAT AG 12

( 2 ) INFORMATION FOR SEQ ID NO:5:

( i ) SEQUENCE CHARACTERISTICS:
        ( A ) LENGTH: 13 base pairs
        ( B ) TYPE: nucleic acid
        ( C ) STRANDEDNESS: unknown
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:5:

CGAATTCAAG CTT 13

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:6:

AAGCTTGAAT TCGACGT                                                                                              17

(2) INFORMATION FOR SEQ ID NO:7:

(i) SEQUENCE CHARACTERISTICS:
        (A) LENGTH: 14 amino acids
        (B) TYPE: amino acid
        (C) STRANDEDNESS: unknown
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:7:

Met His His His His His His Gly Thr Asp Asp Asp Asp Lys
1               5                   10

(2) INFORMATION FOR SEQ ID NO:8:

(i) SEQUENCE CHARACTERISTICS:
        (A) LENGTH: 16 amino acids
        (B) TYPE: amino acid
        (C) STRANDEDNESS: unknown
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:8:

Met His His His His His His Gly Thr Asp Asp Asp Lys Asn Gly
1               5                   10                  15

(2) INFORMATION FOR SEQ ID NO:9:

(i) SEQUENCE CHARACTERISTICS:
        (A) LENGTH: 20 amino acids
        (B) TYPE: amino acid
        (C) STRANDEDNESS: unknown
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:9:

Tyr Glu Val Ile Tyr Val Asp Asp Pro Cys Glu Asp Ser Asp Cys Glu
1               5                   10                  15

Asp Gly Asn Lys
            20

(2) INFORMATION FOR SEQ ID NO:10:

(i) SEQUENCE CHARACTERISTICS:
        (A) LENGTH: 32 base pairs
        (B) TYPE: nucleic acid
        (C) STRANDEDNESS: unknown
        (D) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:10:

AACTCGAGGA TCCAAGCTTT TTTTTTTTT TT 32

( 2 ) INFORMATION FOR SEQ ID NO:11:

( i ) SEQUENCE CHARACTERISTICS:
                ( A ) LENGTH: 39 base pairs
                ( B ) TYPE: nucleic acid
                ( C ) STRANDEDNESS: unknown
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:11:

CCGAATTCAT ATGTAYGARG TNATNTAYGT NGAYGAYCC 39

( 2 ) INFORMATION FOR SEQ ID NO:12:

( i ) SEQUENCE CHARACTERISTICS:
                ( A ) LENGTH: 9 amino acids
                ( B ) TYPE: amino acid
                ( C ) STRANDEDNESS: unknown
                ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:12:

Tyr Glu Val Ile Tyr Val Asp Asp Pro
        1               5

( 2 ) INFORMATION FOR SEQ ID NO:13:

( i ) SEQUENCE CHARACTERISTICS:
                ( A ) LENGTH: 19 base pairs
                ( B ) TYPE: nucleic acid
                ( C ) STRANDEDNESS: unknown
                ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:13:

GAYTGYGARG AYGGNAAYA 19

( 2 ) INFORMATION FOR SEQ ID NO:14:

( i ) SEQUENCE CHARACTERISTICS:
                ( A ) LENGTH: 15 base pairs
                ( B ) TYPE: nucleic acid
                ( C ) STRANDEDNESS: unknown
                ( D ) TOPOLOGY: linear ( i i ) MOLECULE TYPE: DNA (genomic)

-continued ( i i i ) HYPOTHETICAL: NO ( i v ) ANTI-SENSE: NO ( x i ) SEQUENCE DESCRIPTION: SEQ ID NO:14:

GTCCTATGTT TGTAT                                                                               15

( 2 ) INFORMATION FOR SEQ ID NO:15:

( i ) SEQUENCE CHARACTERISTICS:
        ( A ) LENGTH: 12 base pairs
        ( B ) TYPE: nucleic acid
        ( C ) STRANDEDNESS: unknown
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:15:

ATACAAACAT AG                                                                                  12

( 2 ) INFORMATION FOR SEQ ID NO:16:

( i ) SEQUENCE CHARACTERISTICS:
        ( A ) LENGTH: 13 base pairs
        ( B ) TYPE: nucleic acid
        ( C ) STRANDEDNESS: unknown
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:16:

CGAATTCAAG CTT                                                                                 13

( 2 ) INFORMATION FOR SEQ ID NO:17:

( i ) SEQUENCE CHARACTERISTICS:
        ( A ) LENGTH: 17 base pairs
        ( B ) TYPE: nucleic acid
        ( C ) STRANDEDNESS: unknown
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:17:

AAGCTTGAAT TCGACGT                                                                             17

( 2 ) INFORMATION FOR SEQ ID NO:18:

( i ) SEQUENCE CHARACTERISTICS:
        ( A ) LENGTH: 63 amino acids
        ( B ) TYPE: amino acid
        ( C ) STRANDEDNESS: unknown
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:18:

| Met | Ala | Thr | Lys | Ala | Ala | Ser | Val | Leu | Lys | Gly | Asp | Gly | Pro | Val | Gln |
|---|---|---|---|---|---|---|---|---|---|---|---|---|---|---|---|
| 1 | | | | 5 | | | | | 10 | | | | | 15 | |
| Gly | Ile | Ile | Asn | Phe | Glu | Gln | Lys | Glu | Ser | Asp | Gly | Pro | Val | Lys | Val |
| | | | 20 | | | | 25 | | | | | 30 | | | |
| Trp | Gly | Ser | Ile | Lys | Gly | Leu | Thr | Glu | Gly | Leu | His | Gly | Phe | His | Val |
| | | 35 | | | | | 40 | | | | | 45 | | | |
| His | Glu | Phe | Gly | Asp | Asn | Thr | Ala | Gly | Ser | Thr | Ser | Ala | Gly | Pro | |
| | 50 | | | | | 55 | | | | | 60 | | | | |

( 2 ) INFORMATION FOR SEQ ID NO:19:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:19:

| Met | His | His | His | His | His | His | Gly | Thr | Asp | Asp | Asp | Asp | Lys |
|---|---|---|---|---|---|---|---|---|---|---|---|---|---|
| 1 | | | | 5 | | | | | 10 | | | | |

( 2 ) INFORMATION FOR SEQ ID NO:20:

( i ) SEQUENCE CHARACTERISTICS:
        ( A ) LENGTH: 14 amino acids
        ( B ) TYPE: amino acid
        ( C ) STRANDEDNESS: unknown
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:20:

| Met | His | His | His | His | His | His | Gly | Thr | Asp | Asp | Asp | Asp | Lys |
|---|---|---|---|---|---|---|---|---|---|---|---|---|---|
| 1 | | | | 5 | | | | | 10 | | | | |

( 2 ) INFORMATION FOR SEQ ID NO:21:

( i ) SEQUENCE CHARACTERISTICS:
        ( A ) LENGTH: 16 amino acids
        ( B ) TYPE: amino acid
        ( C ) STRANDEDNESS: unknown
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:21:

```
Met  His  His  His  His  His  His  Gly  Thr  Asp  Asp  Asp  Asp  Lys  Asn  Gly
 1                  5                   10                       15
```

( 2 ) INFORMATION FOR SEQ ID NO:22:

( i ) SEQUENCE CHARACTERISTICS:
        ( A ) LENGTH: 94 amino acids
        ( B ) TYPE: amino acid
        ( C ) STRANDEDNESS: unknown
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( i x ) FEATURE:
        ( A ) NAME/KEY: Protein
        ( B ) LOCATION: 1..94

( x i ) SEQUENCE DESCRIPTION: SEQ ID NO:22:

```
Tyr  Glu  Val  Met  Tyr  Val  Asp  Asp  Pro  Cys  Glu  Asp  Ser  Asp  Cys  Glu
 1                   5                   10                       15

Asp  Gly  Asn  Lys  Cys  Ser  Pro  Val  Thr  Asn  Glu  Cys  Asp  Cys  Ser  Pro
               20                   25                       30

Val  Arg  Cys  Arg  Leu  His  Cys  Asn  Phe  Xaa  Tyr  Val  Lys  Asp  Ser  Asn
          35                   40                       45

Gly  Cys  Glu  Thr  Cys  Ala  Cys  Xaa  Xaa  Xaa  Xaa  Xaa  Glu  Pro  Lys  Cys
     50                   55                       60

Lys  His  Lys  Asn  Cys  Ser  Thr  Gly  His  His  Cys  Asn  Lys  Leu  Thr  Asn
65                       70                       75                       80

Lys  Cys  Xaa  Xaa  Xaa  Glu  Leu  Lys  Lys  Gln  Arg  Arg  Met  Gly
                    85                        90
```

( 2 ) INFORMATION FOR SEQ ID NO:23:

( i ) SEQUENCE CHARACTERISTICS:
        ( A ) LENGTH: 118 amino acids
        ( B ) TYPE: amino acid
        ( C ) STRANDEDNESS: unknown
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( i x ) FEATURE:
        ( A ) NAME/KEY: Protein
        ( B ) LOCATION:

( x i ) SEQUENCE DESCRIPTION: SEQ ID NO:23:

```
Lys  Phe  Trp  Thr  Asn  Phe  Arg  Val  Thr  Phe  Thr  Ser  Ile  Leu  Gly  Ile
 1                   5                   10                       15

Leu  Phe  Val  Cys  Glu  Ile  Leu  Ser  Tyr  Glu  Val  Ile  Tyr  Val  Asp  Asp
               20                   25                       30

Pro  Cys  Glu  Asp  Ser  Asp  Cys  Glu  Asp  Gly  Asn  Lys  Cys  Ser  Pro  Val
          35                   40                       45

Thr  Asn  Glu  Cys  Asp  Cys  Ser  Pro  Val  Arg  Cys  Arg  Leu  His  Cys  Asn
     50                   55                       60

Phe  Xaa  Tyr  Val  Lys  Asp  Ser  Asn  Gly  Cys  Glu  Thr  Cys  Ala  Cys  Xaa
```

|  | 65 |  |  |  | 70 |  |  |  | 75 |  |  |  | 80 |
|---|---|---|---|---|---|---|---|---|---|---|---|---|---|
| Xaa | Xaa | Xaa | Xaa | Glu | Pro | Lys | Cys | Lys | His | Lys | Asn | Cys | Pro | Thr | Gly |
|  |  |  |  | 85 |  |  |  |  | 90 |  |  |  |  | 95 |
| His | His | Cys | Asn | Lys | Leu | Thr | Asn | Lys | Cys | Xaa | Xaa | Xaa | Glu | Leu | Lys |
|  |  |  | 100 |  |  |  |  | 105 |  |  |  | 110 |  |  |
| Lys | Gln | Arg | Arg | Met | Gly |
|  |  |  | 115 |  |  |

(2) INFORMATION FOR SEQ ID NO:24:

(i) SEQUENCE CHARACTERISTICS:
        (A) LENGTH: 119 amino acids
        (B) TYPE: amino acid
        (C) STRANDEDNESS: unknown
        (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:24:

| Glu | Gly | Pro | Phe | Gly | Pro | Gly | Cys | Glu | Glu | Ala | Gly | Cys | Pro | Glu | Gly |
|---|---|---|---|---|---|---|---|---|---|---|---|---|---|---|---|
| 1 |  |  |  | 5 |  |  |  |  | 10 |  |  |  |  | 15 |  |
| Ser | Ala | Cys | Asn | Ile | Ile | Thr | Asp | Arg | Cys | Thr | Cys | Ser | Gly | Val | Arg |
|  |  |  | 20 |  |  |  |  | 25 |  |  |  | 30 |  |  |  |
| Cys | Arg | Met | His | Cys | Pro | His | Gly | Phe | Gln | Arg | Ser | Arg | Tyr | Gly | Cys |
|  |  | 35 |  |  |  |  | 40 |  |  |  |  | 45 |  |  |  |
| Glu | Phe | Cys | Lys | Cys | Arg | Leu | Glu | Pro | Met | Lys | Ala | Thr | Cys | Asp | Ile |
|  | 50 |  |  |  |  | 55 |  |  |  |  | 60 |  |  |  |  |
| Ser | Glu | Cys | Pro | Glu | Gly | Met | Met | Cys | Ser | Arg | Leu | Thr | Asn | Lys | Cys |
| 65 |  |  |  |  | 70 |  |  |  |  | 75 |  |  |  |  | 80 |
| Asp | Cys | Lys | Ile | Asp | Ile | Asn | Cys | Arg | Lys | Thr | Cys | Pro | Asn | Gly | Leu |
|  |  |  |  | 85 |  |  |  |  | 90 |  |  |  |  | 95 |  |
| Lys | Arg | Asp | Lys | Leu | Gly | Cys | Glu | Tyr | Cys | Glu | Cys | Arg | Pro | Lys | Arg |
|  |  |  | 100 |  |  |  |  | 105 |  |  |  | 110 |  |  |  |
| Lys | Leu | Ile | Pro | Arg | Leu | Ser |
|  |  |  | 115 |  |  |  |

(2) INFORMATION FOR SEQ ID NO:25:

(i) SEQUENCE CHARACTERISTICS:
        (A) LENGTH: 469 base pairs
        (B) TYPE: nucleic acid
        (C) STRANDEDNESS: unknown
        (D) TOPOLOGY: linear (ii) MOLECULE TYPE: DNA (genomic)

(iii) HYPOTHETICAL: NO (iv) ANTI-SENSE: NO (xi) SEQUENCE DESCRIPTION: SEQ ID NO:25:

```
GGAATTCATA TGTATGAGGT GATGTATGTG GACGATCCAT GTGAGGATTC AGACTGTGAA      60
GATGGAAACA AATGCAGTCC TGTGACCAAT GAATGCGATT GCTCTCCTGT GCGATGCAGA     120
TTGCATTGCA ATTTTTACGT CAAAGACAGT AATGGCTGTG AGACATGCGC TTGTGAGCCT     180
AAATGCAAGC ATAAAAATTG TTCAACTGGC CATCACTGCA ACAAATTGAC AAACAAGTGT     240
GAATTAAAAA AGCAACGAAG AATGGGATAG ACCAAAATAT AAAAAAAAAG AAAGAAGCTG     300
```

| AGAAAAAAG | ATTCCCTGGA | GATTCTCTGA | CGATAAATTA | GCAACATATT | GACTTACTTA | 360 |
| TTCGTAGTTC | CGTTAATAAA | CATGGTTTCC | TAAATAAATA | TTGAAGAAGA | ACTATATTTT | 420 |
| ATTGTTCGCA | TATCAACATT | CAAAATGTCA | AAAAAAAAA | AAAAAAAA | | 469 |

( 2 ) INFORMATION FOR SEQ ID NO:26:

( i ) SEQUENCE CHARACTERISTICS:
        ( A ) LENGTH: 153 amino acids
        ( B ) TYPE: amino acid
        ( C ) STRANDEDNESS: unknown
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:26:

```
Met Tyr Glu Val Met Tyr Val Asp Asp Pro Cys Glu Asp Ser Asp Cys
  1               5                  10                  15
Glu Asp Gly Asn Lys Cys Ser Pro Val Thr Asn Glu Cys Asp Cys Ser
                 20                  25                  30
Pro Val Arg Cys Arg Leu His Cys Asn Phe Tyr Val Lys Asp Ser Asn
             35                  40                  45
Gly Cys Glu Thr Cys Ala Cys Glu Pro Lys Cys Lys His Lys Asn Cys
     50                  55                  60
Ser Thr Gly His His Cys Asn Lys Leu Thr Asn Lys Cys Glu Leu Lys
 65                  70                  75                  80
Lys Gln Arg Arg Met Gly Xaa Thr Lys Ile Xaa Lys Lys Arg Lys Lys
                 85                  90                  95
Leu Arg Lys Lys Asp Ser Leu Glu Ile Leu Xaa Arg Xaa Ile Ser Asn
                100                 105                 110
Ile Leu Thr Tyr Leu Phe Val Val Pro Leu Ile Asn Met Val Ser Xaa
             115                 120                 125
Ile Asn Ile Glu Glu Glu Leu Tyr Phe Ile Val Arg Ile Ser Thr Phe
         130                 135                 140
Lys Met Ser Lys Lys Lys Lys Lys Lys
145                 150
```

( 2 ) INFORMATION FOR SEQ ID NO:27:

( i ) SEQUENCE CHARACTERISTICS:
        ( A ) LENGTH: 684 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:27:

| GAATTCGTGA | ATTCAACATT | TCCACACATA | TCAAAGTAAT | TTTTTCTAA | TAACTCATGA | 60 |
| GGGGTTCTCT | GAGNTGCCTA | CATTCCAATT | TAAGATCAAA | TTTACAACTT | TGGCACATTT | 120 |
| TTGAATAAAG | GAAGCAGGAT | GAAATTCTGG | ACGAATTTTC | GTGTCACTTT | CACTTCCATT | 180 |
| TTGGGAATTT | TATTCGTGTG | CGAAATTCTA | TCGTACGAAG | TGATATACGT | GGATGATCCA | 240 |

```
TGTGAGGATT  CAGACTGTGA  AGATGGAAAC  AAATGCAGTC  CTGTGACCAA  TGAATGCGAT    300

TGCTCTCCTG  TGCGATGCAG  ATTGCATTGC  AATTTTTACG  TCAAAGACAG  TAATGGCTGT    360

GAGACATGCG  CTTGTGAGCC  TAAATGCAAG  CATAAAAATT  GTCCAACTGG  CCATCACTGC    420

AACAAATTGA  CAAACAAGTG  TGAATTAAAA  AAGCAACGAA  GAATGGGATA  GACCAAAATA    480

TAAAAATAAA  GAAAGAAGCT  GAGAAAAGAT  TCCCTAGAGA  TTCTCTGACG  ATAAATTGGC    540

AACATATGTT  GTCTTACTCA  TTCATAATAC  CGTAAATAAA  CATGGTTCCT  AATAATATTG    600

AAGATAAATA  TATTTTATCG  TTCGCATATC  AACATTCAAA  AAAAAAAAA   AAAAAAAAA     660

AAAAAAAAAA  AAAAAAACT   CGAG                                              684
```

(2) INFORMATION FOR SEQ ID NO:28:

(i) SEQUENCE CHARACTERISTICS:
      (A) LENGTH: 182 amino acids
      (B) TYPE: amino acid
      (C) STRANDEDNESS: unknown
      (D) TOPOLOGY: linear (ii) MOLECULE TYPE: protein (iii) HYPOTHETICAL: NO (iv) ANTI-SENSE: NO (v) FRAGMENT TYPE: N-terminal (xi) SEQUENCE DESCRIPTION: SEQ ID NO:28:

```
Met Lys Phe Trp Thr Asn Phe Arg Val Thr Phe Thr Ser Ile Leu Gly
 1           5                  10                  15

Ile Leu Phe Val Cys Glu Ile Leu Ser Tyr Glu Val Ile Tyr Val Asp
            20                  25                  30

Asp Pro Cys Glu Asp Ser Asp Cys Glu Asp Gly Asn Lys Cys Ser Pro
            35                  40                  45

Val Thr Asn Glu Cys Asp Cys Ser Pro Val Arg Cys Arg Leu His Cys
        50                  55                  60

Asn Phe Tyr Val Lys Asp Ser Asn Gly Cys Glu Thr Cys Ala Cys Glu
 65                  70                  75                  80

Pro Lys Cys Lys His Lys Asn Cys Pro Thr Gly His His Cys Asn Lys
                    85                  90                  95

Leu Thr Asn Lys Cys Glu Leu Lys Lys Gln Arg Arg Met Gly Xaa Thr
                100                 105                 110

Lys Ile Xaa Lys Xaa Arg Lys Lys Leu Arg Lys Asp Ser Leu Glu Ile
            115                 120                 125

Leu Xaa Arg Xaa Ile Gly Asn Ile Cys Cys Leu Thr His Ser Xaa Tyr
    130                 135                 140

Arg Lys Xaa Thr Trp Phe Leu Ile Ile Leu Lys Ile Asn Ile Phe Tyr
145                 150                 155                 160

Arg Ser His Ile Asn Ile Gln Lys Lys Lys Lys Lys Lys Lys Lys Lys
                165                 170                 175

Lys Lys Lys Lys Leu Glu
            180
```